US012573202B2

(12) United States Patent
Kurfirst

(10) Patent No.: US 12,573,202 B2
(45) Date of Patent: Mar. 10, 2026

(54) SYSTEMS AND METHODS FOR USING VARIABLE INK DETECTION TO DETECT ENVIRONMENTAL EXPOSURE ON PRODUCTS

(71) Applicant: CVS Pharmacy, Inc., Woonsocket, RI (US)

(72) Inventor: Dwayne Kurfirst, Woonsocket, RI (US)

(73) Assignee: CVS Pharmacy, Inc., Woonsocket, RI (US)

(*) Notice: Subject to any disclaimer, the term of this patent is extended or adjusted under 35 U.S.C. 154(b) by 301 days.

(21) Appl. No.: 18/218,285

(22) Filed: Jul. 5, 2023

(65) Prior Publication Data

US 2025/0014345 A1    Jan. 9, 2025

(51) Int. Cl.
| | |
|---|---|
| *G06V 20/50* | (2022.01) |
| *G01K 11/12* | (2021.01) |
| *G01N 21/64* | (2006.01) |
| *G01N 33/00* | (2006.01) |
| *G06Q 30/018* | (2023.01) |
| *G06V 10/774* | (2022.01) |

(52) U.S. Cl.
CPC .............. *G06V 20/50* (2022.01); *G01K 11/12* (2013.01); *G01N 21/6428* (2013.01); *G01N 21/6456* (2013.01); *G01N 33/0001* (2013.01); *G06Q 30/018* (2013.01); *G06V 10/774* (2022.01); *G01N 2021/6439* (2013.01)

(58) Field of Classification Search
None
See application file for complete search history.

(56) References Cited

U.S. PATENT DOCUMENTS

| | | | |
|---|---|---|---|
| 3,471,422 A | 10/1969 | Edlein et al. | |
| 4,240,926 A | 12/1980 | McNeely | |

(Continued)

FOREIGN PATENT DOCUMENTS

| | | |
|---|---|---|
| CN | 101885391 A | 11/2010 |
| GB | 2 272 861 A | 6/1994 |

(Continued)

OTHER PUBLICATIONS

Doran et al. "Color-Changing Inks Respond to the Environment," https://www.cnn.com/2017/03/27/europe/unseen-ink/index.html (Apr. 11, 2017).

(Continued)

*Primary Examiner* — Helen Zong
(74) *Attorney, Agent, or Firm* — Leydig, Voit & Mayer, Ltd.

(57)    ABSTRACT

A method is provided, the method including obtaining one or more vision machine learning—artificial intelligence (ML-AI) models associated with a product and obtaining one or more images of a product label of the product. The product label indicates a variable ink that changes colors based on environmental aspects. The method also includes determining condition information indicating a status of the product label based on the one or more vision ML-AI models and the one or more images of the product label indicating the variable ink, and outputting an indicator indicating the status of the product label based on the condition information.

20 Claims, 8 Drawing Sheets

(56) References Cited

U.S. PATENT DOCUMENTS

| | | | |
|---|---|---|---|
| 4,603,030 A | 7/1986 | McCarthy | |
| 5,989,700 A | 11/1999 | Krivopal | |
| 6,298,331 B1 * | 10/2001 | Walker | G06Q 20/12 |
| | | | 705/16 |
| 7,017,623 B2 | 3/2006 | Tribble et al. | |
| 7,515,262 B2 | 4/2009 | Sirat et al. | |
| 8,959,029 B2 | 2/2015 | Jones et al. | |
| 9,016,193 B2 * | 4/2015 | Minvielle | A23B 2/003 |
| | | | 235/375 |
| 9,965,730 B2 * | 5/2018 | Hance | G06Q 10/087 |
| 10,055,837 B2 | 8/2018 | Lee et al. | |
| 10,140,492 B1 | 11/2018 | Nair | |
| 10,474,858 B2 | 11/2019 | Davis et al. | |
| 10,733,913 B2 | 8/2020 | Atkinson et al. | |
| 10,801,900 B2 | 10/2020 | Poirier | |
| 10,872,488 B2 | 12/2020 | Ladrón et al. | |
| 11,105,690 B2 | 8/2021 | Tada et al. | |
| 11,455,483 B2 * | 9/2022 | Prusik | G06K 19/0614 |
| 2005/0031838 A1 | 2/2005 | Lagunowich et al. | |
| 2012/0104278 A1 * | 5/2012 | Downing | G01N 21/6428 |
| | | | 250/200 |
| 2014/0370344 A1 * | 12/2014 | Lovelace | H02J 7/0069 |
| | | | 429/185 |
| 2018/0020145 A1 * | 1/2018 | Kotfis | H04N 23/72 |
| 2019/0316948 A1 | 10/2019 | Karol et al. | |
| 2020/0234019 A1 * | 7/2020 | Prusik | G06K 19/06046 |
| 2020/0281254 A1 | 9/2020 | Rogan | |
| 2021/0001377 A1 | 1/2021 | Sutton | |
| 2021/0027608 A1 * | 1/2021 | Shakedd | G08B 21/24 |
| 2021/0097364 A1 * | 4/2021 | Salsberg | G06K 19/07788 |
| 2021/0375456 A1 | 12/2021 | Kurfirst | |
| 2021/0389190 A1 * | 12/2021 | Nemet | G09F 3/0294 |
| 2023/0053572 A1 * | 2/2023 | Yang | H04W 60/04 |
| 2023/0178212 A1 * | 6/2023 | Gong | G16H 20/60 |
| | | | 705/2 |
| 2023/0185923 A1 * | 6/2023 | Givental | G06N 3/08 |
| | | | 706/12 |
| 2023/0267273 A1 * | 8/2023 | Theriappan | G06N 5/022 |
| | | | 704/9 |
| 2025/0010193 A1 * | 1/2025 | Wang | G06F 3/0484 |
| 2025/0127997 A1 * | 4/2025 | Seyed Vahedein | G16H 40/63 |

FOREIGN PATENT DOCUMENTS

| | | | |
|---|---|---|---|
| GB | 2 478 573 A | 9/2011 | |
| KR | 10-1123626 B1 | 4/2012 | |
| WO | WO 2011/037932 A1 | 3/2011 | |
| WO | WO 2014/057032 A1 | 4/2014 | |

OTHER PUBLICATIONS

Grimaud et al., "Illuminating Odors: When Optogenetics Brings to Light Unexpected Olfactory Abilities," *Learning & Memory*, 23(6), 249-254 (2016).

Haupert, Laura "Why Odors Get Worse as Weather Warms," https://www.linkedin.com/pulse/why-odors-get-worse-weather-warms-laura-haupert-ph-d-/ (May 16, 2019).

Jin et al., "Photo-Chromeleon: Re-Programmable Multi-Color Textures Using Photochromic Dyes" *UIST* '19, New Orleans, LA, USA (Oct. 20-23, 2019).

Kramer, Jillian "Color-Changing Ink Turns Clothes into Giant Chemical Sensors," *Scientific American* (Jul. 3, 2020).

"Light Can Change Flavor, Scent Volatiles in Plants and Fruits, Study Finds," University of Florida, phys.org (Jul. 23, 2013).

"Paper or Ink that Naturally Degrades in a Month or Less?" Worldbuilding, https://worldbuilding.stackexchange.com/questions/219298/paper-or-ink-that naturally-degraes-in-a-month-or-less (Accessed Feb. 15, 2023).

"Trust Made Simple," https:/ennoventure.com/ (Accessed Feb. 15, 2023).

Wang, Ziyi "Degradation Modeling of Ink Fading and Diffusion of Printed Images," Rutgers, The State University of New Jersey (2020).

Wnuk et al. "Hot and Cold Smells: Odor-Temperature Associations across Cultures," *Frontiers in Psychology*, vol. 8 (Aug. 2017).

* cited by examiner

402

Obtain one or more vision machine learning -- artificial intelligence
(ML -- AI) models associated with a product.

404

Obtain one or more images of a product label of the product, wherein the
product label indicates a variable ink that changes colors based on
environmental aspects.

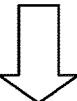

406

Determine condition information indicating a status of the product label
based on the one or more vision ML -- AI models and the one or more
images of the product label indicating the variable ink.

408

Output an indicator indicating the status of the product label based on the
condition information.

Figure 5:
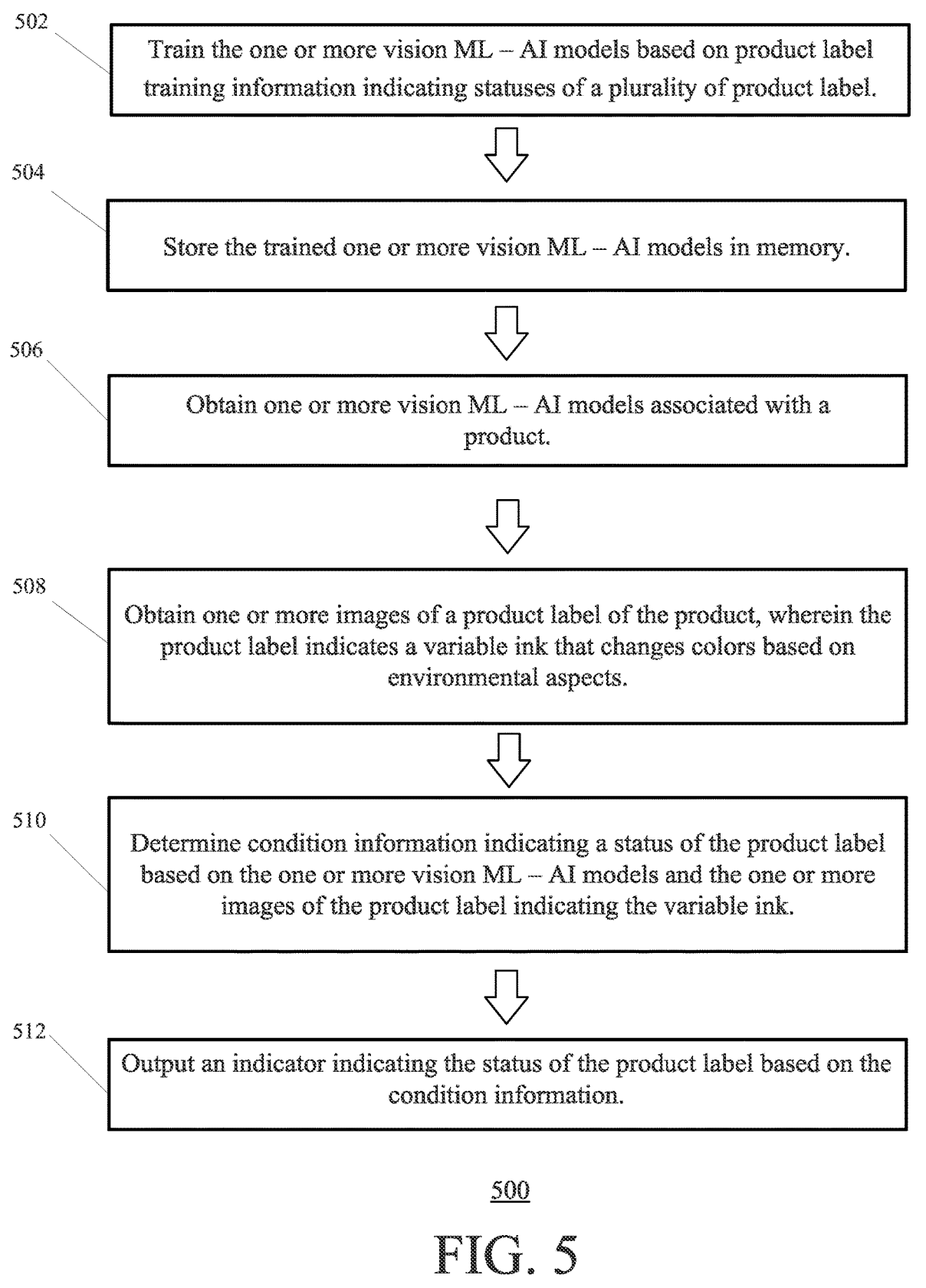

502 — Train the one or more vision ML – AI models based on product label training information indicating statuses of a plurality of product label.

504 — Store the trained one or more vision ML – AI models in memory.

506 — Obtain one or more vision ML – AI models associated with a product.

508 — Obtain one or more images of a product label of the product, wherein the product label indicates a variable ink that changes colors based on environmental aspects.

510 — Determine condition information indicating a status of the product label based on the one or more vision ML – AI models and the one or more images of the product label indicating the variable ink.

512 — Output an indicator indicating the status of the product label based on the condition information.

SYSTEMS AND METHODS FOR USING VARIABLE INK DETECTION TO DETECT ENVIRONMENTAL EXPOSURE ON PRODUCTS

BACKGROUND

In some instances, enterprise organizations may seek to verify if one or more products that they are selling have been kept under optimal conditions. For instance, some products that are exposed to certain environmental conditions can become problematic (e.g., by expiring, spoiling, or deteriorating). To manage inventory and safely retail these products, it may be helpful to verify whether these products, or which specific products, have been exposed to notable environmental conditions. For example, for food products such as frozen food products, if the product reaches a certain temperature (e.g., room temperature), the product may spoil and/or deteriorate in quality. Enterprise organizations may seek to avoid selling such products to consumers, and may seek to track whether the product has been exposed to such environmental conditions. Therefore, there remains a technical need to provide reliable information on the environmental conditions exposed to a product while also reducing the related environmental and maintenance burden.

SUMMARY

In some examples, the present application is directed to determining condition information of a product by determining a status of a variable ink on a product label that is sensitive to environmental changes. For instance, various inks and/or scent markers can exhibit properties that change in response to external stimulus (e.g., light, heat, moisture, electrical charge). By applying these variable inks to a product label, the inks can respond according to the conditions experienced by the product (e.g., amount of light exposure or humidity levels). The variable ink may then achieve an analog recreation of the corresponding internet of things (IoT) device, acting as a visual indicator of the conditions experienced by the product without the need for batteries, wires, or electronic monitoring of the IoT device. Accordingly, the present application may improve sustainability by reducing the environmental burden and maintenance burden of monitoring a product's conditions.

In some instances, to provide for an integrated and/or passive system to assess the conditions of large volumes of products, vision and/or olfactory systems may be installed at relevant, convenient points of the supply chain to monitor the state of the products while the products are moved or located in the normal course of operations. These olfactory and vision systems may be deployed in conjunction with machine learning—artificial intelligence (ML-AI) models to determine the state (e.g., condition and/or status) of the variable ink, and thereby alert a user or inventory system that a product is flagged as improper, or is flagged for review and may need to be reviewed to assess the viability of the product and determine a course of action with respect to the product. Further, once a product has been flagged for review or as improper (e.g., because it is not in a ceiling or floor threshold for proper storage), a message may be sent to a backend server to determine if this product was with other similarly susceptible products. If so, then those other similarly susceptible products may also be flagged for review or as improper.

In one aspect, a system comprising one or more vision capturing devices and one or more sensor system computing devices is provided. The one or more vision capturing devices are configured to obtain one or more images of a product label of a product, wherein the product label indicates a variable ink that changes colors based on environmental aspects. The one or more sensor system computing devices are configured to: access, via an enterprise computing system, one or more first ML-AI models associated with the product; determine condition information indicating a status of the product label based on the one or more first ML-AI models and the one or more images of the product label indicating the variable ink; and provide, to a user device, an indicator indicating the status of the product label based on the condition information.

Examples may include one of the following features, or any combination thereof. For instance, in some examples of the system, the prompt indicates to sell the product at a discounted price or discard the product.

In some instances, the system further comprises one or more olfactory sensors configured to obtain olfactory information indicating a scent of the product, and the one or more sensor system computing devices are further configured to: access, via the enterprise computing system, one or more second ML-AI models associated with the product; and determine the condition information indicating the status of the product label further based on the one or more second ML-AI models and the olfactory information.

In some variations, the variable ink is a thermochromatic ink that changes color based on a temperature range, and product label training information for the one or more first ML-AI models comprises one or more images of thermochromatic ink product labels.

In another aspect, a method is provided. The method comprises obtaining one or more vision machine learning-artificial intelligence (ML-AI) models associated with a product; obtaining one or more images of a product label of the product, wherein the product label indicates a variable ink that changes colors based on environmental aspects; determining condition information indicating a status of the product label based on the one or more vision ML-AI models and the one or more images of the product label indicating the variable ink; and outputting an indicator indicating the status of the product label based on the condition information.

Examples may include one of the following features, or any combination thereof. For instance, in some examples, outputting the indicator indicating the status of the product label further comprises providing, to a user device, the indicator indicating the status of the product label, wherein the user device causes display of a prompt indicating the status of the product label, wherein the prompt indicates to sell the product at a discounted price or discard the product.

In some variations, the method further comprises obtaining one or more olfactory ML-AI models associated with the product; and obtaining, using one or more olfactory sensors, olfactory information indicating a scent of the product, and determining the condition information indicating the status of the product label is further based on the one or more olfactory ML-AI models and the olfactory information.

In some examples, determining the condition information indicating the status of the product label comprises: inputting one or more representations associated with the one or more images into the one or more vision ML-AI models to determine vision ML-AI information; inputting the olfactory information into the one or more olfactory ML-AI models to determine olfactory ML-AI information; and determining the condition information indicating the status of the product label based on the vision ML-AI information and the olfactory ML-AI information.

In some instances, the vision ML-AI information is a first condition confidence value that is output from the one or more vision ML-AI models, wherein the olfactory ML-AI information is a second condition confidence value that is output from the one or more olfactory ML-AI models, and determining the condition information comprises determining the condition information as a weighted average of the first condition confidence value and the second condition confidence value.

In some variations, the method further comprises training the one or more vision ML-AI models based on product label training information indicating statuses of a plurality of product labels; and storing the trained one or more vision ML-AI models in memory, and obtaining the one or more vision ML-AI models comprises retrieving the trained one or more vision ML-AI models from memory.

In some examples, the product label training information comprises a plurality of images of the plurality of product labels, wherein at least one of the plurality of images indicates a baseline condition of a first product label prior to being applied to any products, and the one or more vision ML-AI models comprises an unsupervised ML-AI model.

In some instances, the variable ink is a photochromic ink that changes colors based on temperatures exposed to sunlight, and the product label training information comprises one or more images of photochromic ink product labels.

In some variations, the variable ink is a glow-in-the-dark ink that changes colors based on absorbing light and glowing in darkness, and the product label training information comprises one or more images of glow-in-the-dark ink product labels.

In some examples, the variable ink is a fluorescing ink that absorbs ultraviolet (UV) light and re-emits the UV light within a visible spectrum, and the product label training information comprises one or more images of fluorescing ink product labels.

In some instances, the one or more vision ML-AI models comprise a pharmaceutical vision ML-AI model associated with a pharmaceutical medication and a retail vision ML-AI model associated with one or more retail items, and the method further comprises: determining, based on the one or more images, whether the product is the one or more retail items or the pharmaceutical medication, and determining the condition information is further based on whether the product is the one or more retail items or the pharmaceutical medication.

In some variations, the one or more vision ML-AI models comprise a first pharmaceutical vision ML-AI model associated with a first type of pharmaceutical medication and a second pharmaceutical vision ML-AI model associated with a second type of pharmaceutical medication, and the method further comprises: training the first pharmaceutical vision ML-AI model based on a plurality of first images of one or more first product labels at a first baseline condition; and training the second pharmaceutical vision ML-AI model based on a plurality of second images of one or more second product labels at a second baseline condition that is different from the first baseline condition.

In some examples, obtaining the one or more vision ML-AI models further comprises receiving, from an enterprise computing system, the one or more vision ML-AI models that are trained by the enterprise computing system, and obtaining the one or more images of the product label comprises capturing the one or more images of the product label.

In some instances, outputting the indicator indicating the status of the product label comprises providing the indicator to the enterprise computing system, and the method further comprises: receiving, from the enterprise computing system, identification information indicating one or more additional products that have the same status as the product.

In some variations, the one or more images comprise a first image of the product label of the product from a first viewpoint and a second image of the product label of the product from a second viewpoint that is different from the first viewpoint.

In yet another aspect, a non-transitory computer-readable medium having processor-executable instructions stored thereon is provided. The processor-executable instructions, when executed by one or more controllers, facilitate: obtaining one or more vision machine learning-artificial intelligence (ML-AI) models associated with a product; obtaining one or more images of a product label of the product, wherein the product label indicates a variable ink that changes colors based on environmental aspects; determining condition information indicating a status of the product label based on the one or more vision ML-AI models and the one or more images of the product label indicating the variable ink; and outputting an indicator indicating the status of the product label based on the condition information.

All examples and features mentioned above may be combined in any technically possible way.

BRIEF DESCRIPTION OF THE DRAWINGS

The subject technology will be described in even greater detail below based on the exemplary figures, but is not limited to the examples. All features described and/or illustrated herein can be used alone or combined in different combinations. The features and advantages of various examples will become apparent by reading the following detailed description with reference to the attached drawings which illustrate the following:

FIG. 4 is an exemplary process for using the exemplary sensing system to determine the status of a product label in accordance with one or more examples of the present application;

FIG. 5 is an exemplary process for using the exemplary sensing system to determine the status of a product label in accordance with one or more examples of the present application;

DETAILED DESCRIPTION

Examples of the presented application will now be described more fully hereinafter with reference to the accompanying FIGS., in which some, but not all, examples of the application are shown. Indeed, the application may be exemplified in different forms and should not be construed as limited to the examples set forth herein; rather, these examples are provided so that the application will satisfy applicable legal requirements. Where possible, any terms expressed in the singular form herein are meant to also include the plural form and vice versa, unless explicitly stated otherwise. Also, as used herein, the term "a" and/or "an" shall mean "one or more" even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on".

Figure 1:
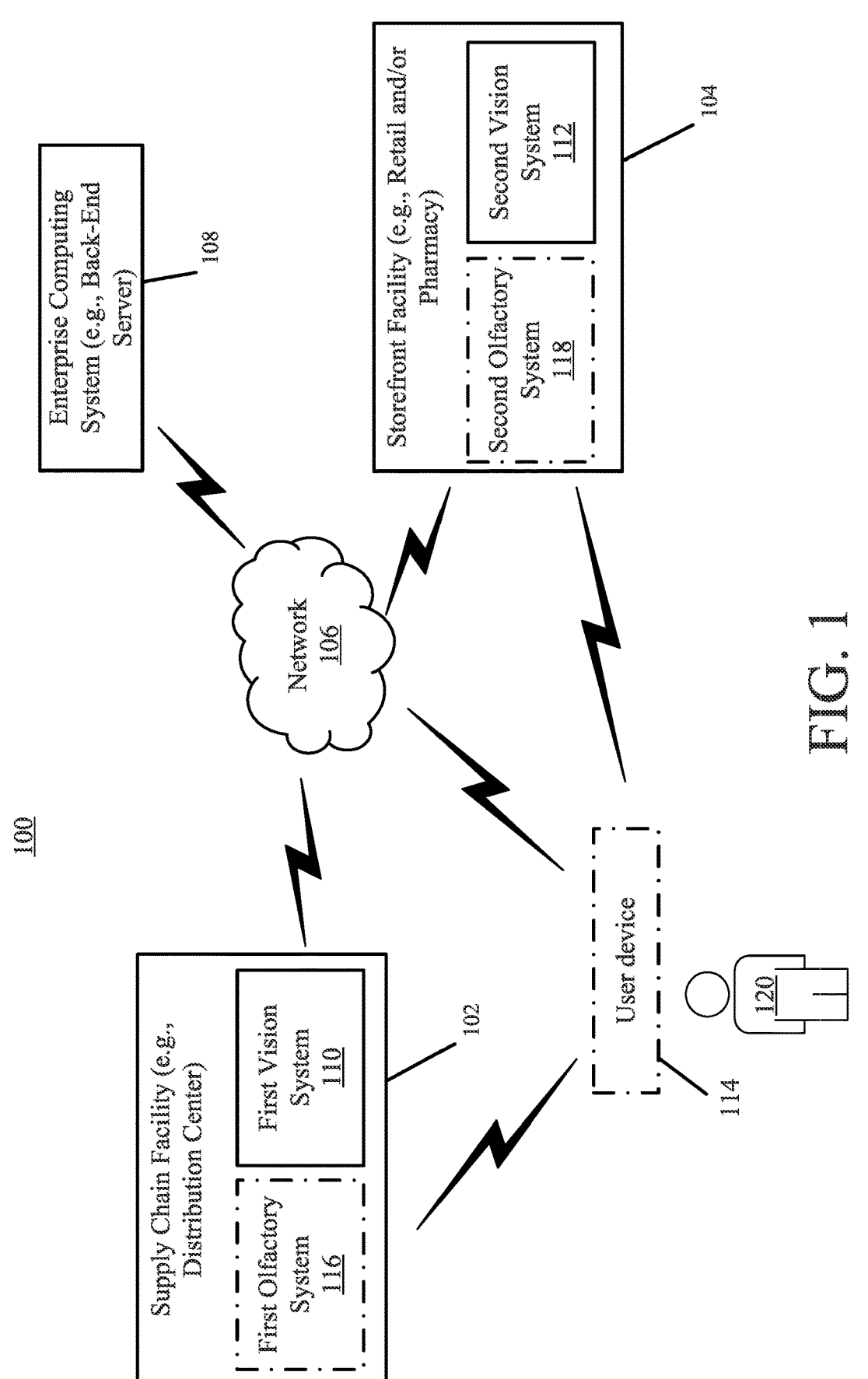
FIG. 1 is a simplified block diagram depicting an exemplary detection environment in accordance with one or more examples of the present application.

Systems, methods, and computer program products are herein disclosed that use one or more sensor systems to determine a status of a product label (e.g., of variable ink on the product label) using one or more ML-AI models. FIG. 1 is a simplified block diagram depicting an exemplary environment in accordance with an example of the present application. The environment 100 includes a supply chain facility 102 (e.g., a distribution center (DC)), a storefront facility 104 (e.g., a retail and/or pharmacy store), an enterprise computing system 108 (e.g., a back-end server), and optionally, a user device 114 and/or user 120. Although the entities within environment 100 may be described below and/or depicted in the FIGS. as being singular entities, it will be appreciated that the entities and functionalities discussed herein may be implemented by and/or include one or more entities.

The entities within the environment 100 such as the supply chain facility 102, the storefront facility 104, the user device 114, and/or the enterprise computing system 108 may be in communication with other systems or facilities within the environment 100 via the network 106. The network 106 may be a global area network (GAN) such as the Internet, a wide area network (WAN), a local area network (LAN), or any other type of network or combination of networks. The network 106 may provide a wireline, wireless, or a combination of wireline and wireless communication between the entities within the environment 100.

The supply chain facility 102 may include a first sensor system (e.g., a first vision system 110 and/or a first olfactory system 116), and the storefront facility 104 may include a second sensor system (e.g., a second vision system 112 and/or a second olfactory system 118). The first vision system 110 may be in communication with the second vision system 112 using the network 106. In some instances, the first and second vision systems 110 and 112 may be similar, including relying on or having similar and/or the same components such as one or more imaging sensors or cameras. The first and second olfactory systems 116 and 118 may also be similar, including or having similar and/or the same components such as one or more olfactory sensors/devices. Additionally, and/or alternatively, the first vision system 110 and/or the second vision system 112 and the user device 114 may communicate with each other and/or other entities within environment 100 (e.g., the enterprise computing system 108 or the user device 114) without using the network 106 (e.g., via communication protocols such as WI-FI or BLUETOOTH).

The enterprise computing system 108 is a computing system that is associated with an enterprise organization. The enterprise organization may be any type of corporation, company, organization, and/or other institution. In some instances, the enterprise organization may own, operate, and/or be otherwise associated with distribution of drugs, medications, food products, objects, items, and/or other products that may be susceptible to environmental conditions. For example, a pharmaceutical product may deteriorate if exposed to certain wavelengths of light and/or if exposed to certain temperatures and/or humidity levels. The enterprise organization may distribute the pharmaceutical product such as obtaining the product from the manufacturer, storing and/or packaging the product in a DC, and providing the product to a third party or commonly owned storefront facility such as pharmacies, retail stores, and/or other types of facilities that a consumer may visit in order to obtain the product.

In some variations, the products may change in condition (e.g., deteriorate), and the first vision system 110, the second vision system 112, the first olfactory system 116, and/or the second olfactory system 118 may be used to determine the condition of the product (e.g., the deteriorated pharmaceutical product). For instance, the pharmaceutical product may have active ingredients that require storage at a certain environmental condition such as refrigerated or in a cool environment. During the summer season, if the pharmaceutical product is left out, the active ingredient may deteriorate and as such, the pharmaceutical product might not be effective. To prevent the sale of ineffective, or the decreased efficiency of, pharmaceutical products, the sensor systems may use ML-AI models to determine the change of the product label of the pharmaceutical product. For instance, the product label may include variable ink that changes based on environmental conditions such as being out in direct sunlight or in a higher temperature environment than standard storage conditions. The sensor systems may detect, flag, and/or perform actions based on the change in variable ink of the product label. While pharmaceutical products are described above, the detection of conditions based on the variable ink may be applied to any type of product associated with the enterprise organization such as food products and/or other types of products.

The enterprise computing system 108 may include one or more ML-AI models such as one or more vision system ML-AI models (e.g., non-product specific vision ML-AI models and/or product-specific vision ML-AI models and/or olfactory ML-AI models). In some instances, the ML-AI models may be generic ML-AI models (e.g., untrained ML-AI models). The enterprise computing system 108 may train the generic ML-AI models prior to providing them to a sensor system (e.g., a sensor system associated with the supply chain facility 102 and/or the storefront facility 104). Additionally, and/or alternatively, the sensor system may train the ML-AI models and/or use the ML-AI models to perform one or more tasks.

The enterprise computing system 108 includes one or more computing devices, computing platforms, systems, servers, and/or other apparatuses capable of performing tasks, functions, and/or other actions for the enterprise organization. The enterprise computing system 108 may be implemented using one or more computing platforms, devices, servers, and/or apparatuses. In some variations, the enterprise computing system 108 may be implemented as engines, software functions, and/or applications. In other words, the functionalities of the enterprise computing system 108 may be implemented as software instructions stored in storage (e.g., memory) and executed by one or more processors.

The supply chain facility 102 may be any facility (e.g., building, residence, shipping and receiving center, structure) that includes computing devices (e.g., a first sensor system that includes the first vision system 110 and/or the first olfactory system 116) that trains and/or uses the ML-AI models such as the vision system ML-AI models and/or olfactory ML-AI models. Additionally, and/or alternatively, the supply chain facility 102 may be a distribution center that obtains the products (e.g., medication, drugs, sanitary goods, food products) from a manufacturer and ships them to a second facility, such as a storefront facility 104 (e.g., a retail facility). The supply chain facilities 102 may also package and/or re-package the products after receiving the products and before shipping the products. In another instance, the supply chain facilities 102 may be a manufacturer that produces and/or packages the products. The supply chain facility 102 may include one or more computing devices or entities that are configured to train the ML-AI models using samples of the product labels. For instance, the supply chain facility 102 may include a first vision system 110. The first vision system 110 may include one or more sensors, image and/or vision capturing devices, and/or other devices. The first vision system 110 may obtain training information from the sensors and/or cameras. Using the training information, the first vision system 110 may train the ML-AI models, and provide the trained ML-AI models to a second vision system 112 and/or the enterprise computing system 108.

Similarly, the supply chain facility 102 may optionally include a first olfactory system 116. When present, the first olfactory system 116 may include sensors, such as olfactory sensors. The first olfactory system 116 may obtain training information from olfactory sensors, alone or in combination with the sensors, cameras, and/or imaging devices of the first vision system 110. Using the training information, the first olfactory system 112 may train the olfactory ML-AI models, and provide the trained ML-AI models to a second olfactory system 118 and/or the enterprise computing system 108. The first vision system 110, the first olfactory system 116, and the training of the ML-AI models will be described in further detail below.

Additionally, and/or alternatively, the first sensor system (e.g., the first vision system 110 and/or the first olfactory system 116) may use the ML-AI models. For example, the first sensor system and/or another entity (e.g., the enterprise computing system 108) may train the ML-AI models. After training, the first sensor system may use the ML-AI models to determine a condition change of a product. For instance, the first sensor system may obtain images and/or video frames of a product label with variable ink that is associated with a product. The first sensor system may provide the information associated with the captured images and/or frames into the trained ML-AI models to determine a status of the product label.

The storefront facility 104 may be any building, storefront, retail, pharmacy, or structure that distributes products (e.g., sanitary goods, food products, pharmaceutical products, clothing) to a consumer. For instance, the enterprise organization may be a pharmacy service and/or retail enterprise organization that provides medications and/or retail products to a consumer, and the storefront facility 104 may stock and shelf these retail products. Based on whether the product is still in good condition, soon to expire, or expired, the storefront facility 104 may stock, remove from stock, discount, or take the product off the shelf. The enterprise organization may own, operate, and/or be associated with the supply chain facility 102 and/or the storefront facility 104. For instance, the supply chain facility 102 may be a distribution center and the storefront facility 104 may be a pharmacy, retail store, and/or other facility that retails the products to the consumer based on the condition of the product.

The storefront facility 104 may include a second sensor system (e.g., a second vision system 112), which may train and/or use the ML-AI models. For instance, the second vision system 112 may obtain the trained ML-AI models from the first vision system 110, the enterprise computing system 108, and/or from local memory, and determine condition information indicating a status of the product label. For instance, the second vision system 112 may include one or more sensors/devices such as an image capturing device. The second vision system 112 may obtain one or more images or representations of a product label of the product using the one or more sensors/devices. Based on inputting the one or more images or representations into the one or more trained ML-AI models, the second vision system 112 may determine visual ML-AI information (e.g., condition information) indicating a status of the product label, which in turn, may indicate a condition of the product. For instance, the condition information may indicate that a variable ink of the product label has undergone a change in color, intensity, etc., which as explained in further detail below, may indicate that the product label has been exposed to a corresponding environmental condition. The second vision system 112 may provide the condition information to another device such as the enterprise computing system 108 and/or perform other actions.

The storefront facility 104 may optionally include a second olfactory system 118. When present, the second olfactory system 118 may obtain the trained olfactory ML-AI models from the first olfactory system 116, the enterprise computing system 108, and/or from local memory, and determine condition information indicating a status of the product label. For instance, the second olfactory system 118 may include one or more olfactory sensors, and may obtain olfactory information alone or in combination with the sensors/devices of the second vision system 112. The second olfactory system 118 may obtain olfactory information indicating a scent of the product, which in turn, may indicate a condition of the product. For instance, the olfactory information indicating a scent of the product has undergone a change in profile, intensity, etc., which as explained in further detail below, may indicate that the product label has been exposed to a corresponding environmental condition. The second olfactory system 118 may provide the condition information to another device such as the enterprise computing system 108 and/or perform other actions.

User 120 may operate, own, and/or otherwise be associated with a user device 114, and the user 120 and user device 114 may be part of the enterprise organization. For instance, the user device 114 may be a mobile phone such as a smartphone that is owned and/or operated by the user 120. The user device 114 may be and/or include, but is not limited to, a desktop, laptop, tablet, mobile device (e.g., smartphone device, or other mobile device), smart watch, IoT device, or any other type of computing device that generally comprises one or more communication components, one or more processing components, and one or more memory components. The user device 114, when present, may be able to execute software applications managed by, in communication with, and/or otherwise associated with the enterprise organization. The software application may be an application that is used by the user device 114 to communicate with the computing devices of the storefront facility 104, the supply chain facility 102, and the enterprise computing system 108. This communication between the user device 114 and the other entities of environment 100 may occur over the network 106. Additionally, and/or alternatively, the user device 114 may communicate with each other and/or other entities within environment 100 without using the network 106 (e.g., via communication protocols such as WI-FI or BLUETOOTH).

The user 120 may provide information to the other entities of environment 100 such as the enterprise computing system 108 and/or the storefront facility 104 and supply chain facility 102 using the user device 114. The user 120 may also receive information from other entities of environment 100 such as the enterprise computing system 108 and/or the storefront facility 104 and supply chain facility 102 using the user device 114. For example, the user device 114 may receive information regarding an indicator of the status of a product label, and the user 120 may take one or more actions in response to the indicator of the status of the product label, such as to discount, stock, or dispose of a product. Before, during, or after taking action in response to the received indicator, the user device 114 may provide information to any other entity of environment 100 regarding the action taken or to be taken.

It will be appreciated that the exemplary environment depicted in FIG. 1 is merely an example, and that the principles discussed herein may also be applicable to other situations—for example, including other types of institutions, organizations, devices, systems, and network configurations. For instance, a single vision system may be distributed across both the supply chain facility 102 and the storefront facility 104, and a single sensor system may perform the functionalities of both the first olfactory system 116 and the first vision system 110 or perform the functionalities of both the first olfactory system 116 and the second olfactory system 118. For instance, the single vision system may train the ML-AI models and use the ML-AI models to determine the condition information. Similarly, the vision systems and the olfactory systems may work separately or in combination to determine the condition information.

As will be described herein, the environment 100 may be used by retail enterprise organizations. However, in other instances, the environment 100 may be used by other types of enterprise organizations such as health care, insurance, and/or other types of enterprise organizations.

Figure 2:
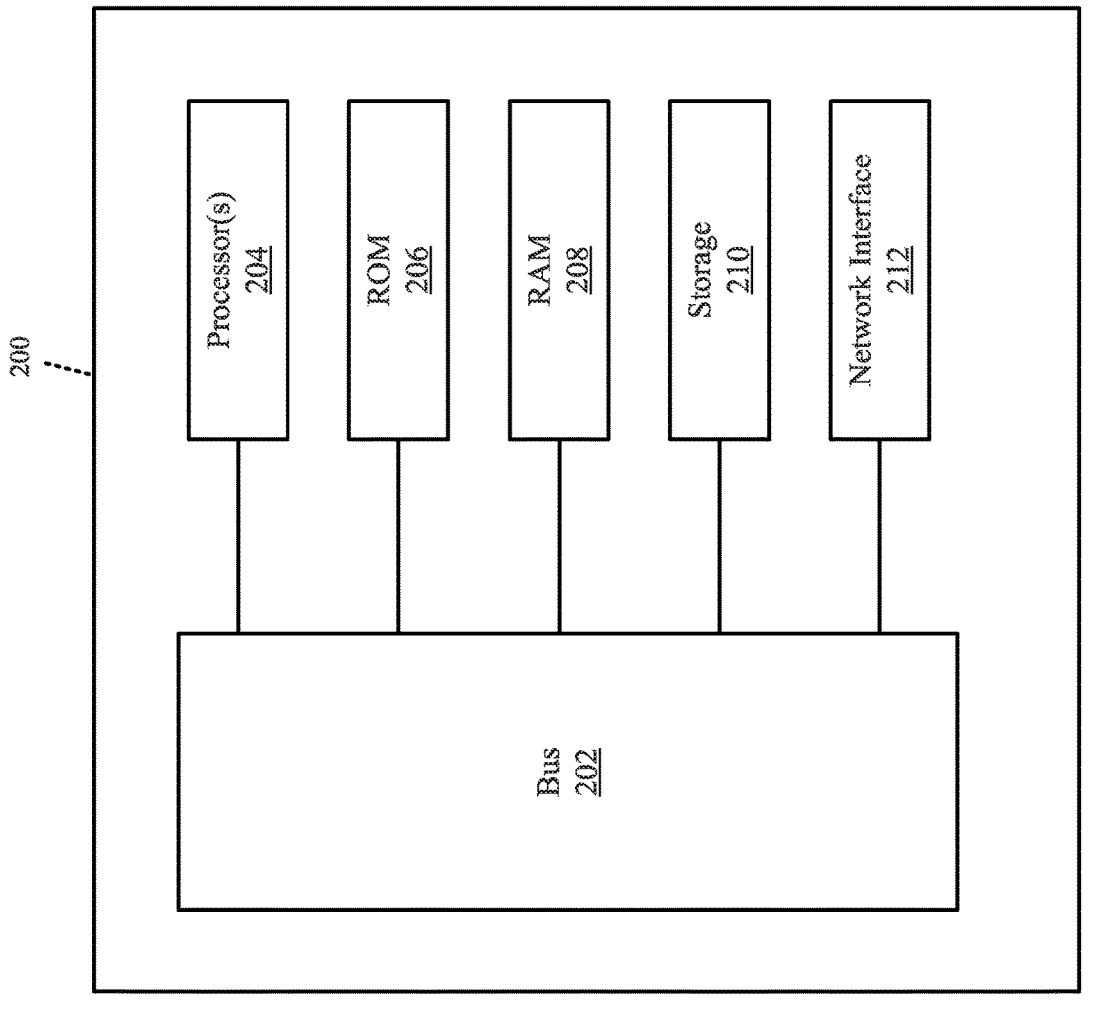
FIG. 2 is a simplified block diagram of one or more devices or systems within the exemplary environment of FIG. 1.

FIG. 2 is a block diagram of an exemplary system and/or device 200 within the environment 100. The device/system 200 includes a processor 204, such as a central processing unit (CPU), controller, and/or logic, that executes computer executable instructions for performing the functions, processes, and/or methods described herein. In some examples, the computer executable instructions are locally stored and accessed from a non-transitory computer readable medium, such as storage 210, which may be a hard drive or flash drive. Read Only Memory (ROM) 206 includes computer executable instructions for initializing the processor 204, while the random-access memory (RAM) 208 is the main memory for loading and processing instructions executed by the processor 204. The network interface 212 may connect to a wired network or cellular network and to a local area network or wide area network, such as the network 106. The device/system 200 may also include a bus 202 that connects the processor 204, ROM 206, RAM 208, storage 210, and/or the network interface 212. The components within the device/system 200 may use the bus 202 to communicate with each other. The components within the device/system 200 are merely exemplary and might not be inclusive of every component within the device/system 200. For example, as will be described below, the first vision system 110, and the second vision system 112, and when present, the first olfactory system 116, and the second olfactory system 118, may include some of the components within the device/system 200 and may also include further components such as one or more sensors and/or devices. Additionally, and/or alternatively, the device/system 200 may further include components that might not be included within every entity of environment 100.

Figure 3:
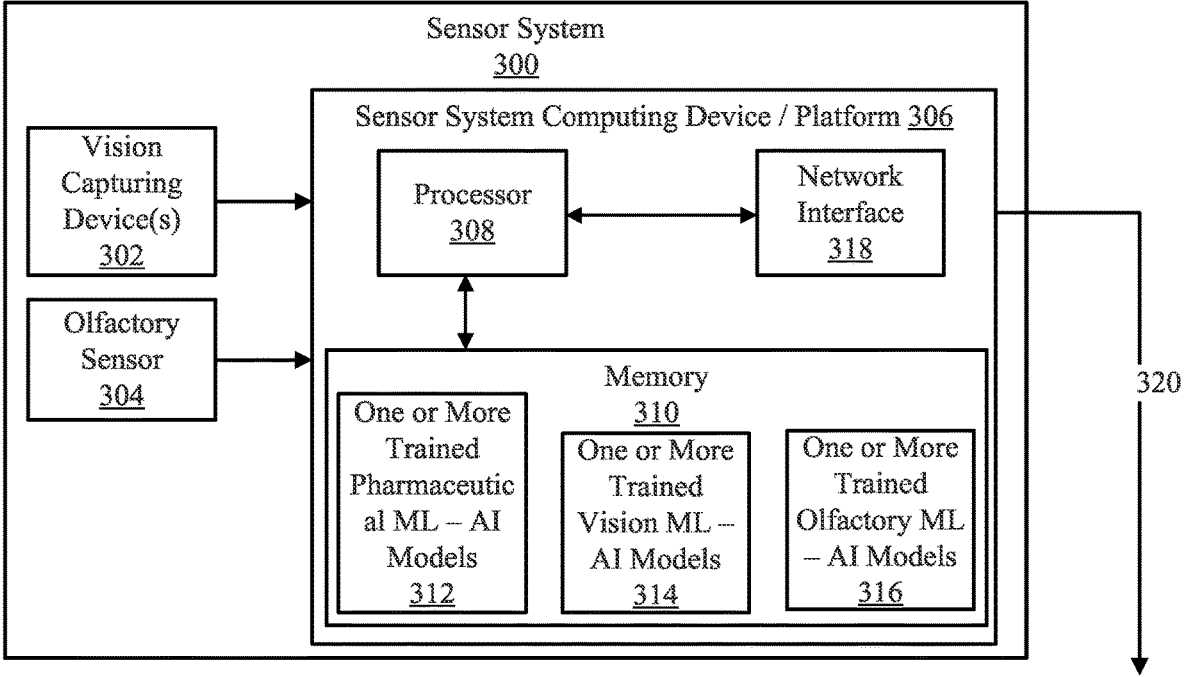
FIG. 3 is a simplified block diagram depicting devices in an exemplary sensing system in accordance with one or more examples of the present application.

FIG. 3 is a simplified block diagram depicting a sensor system 300 in accordance with one or more examples of the present application. For example, the sensor system 300 includes, but is not limited to, vision capturing devices 302 and olfactory sensors 304. The vision capturing devices 302 may collect and/or receive visual information (e.g., images and videos) from an environment of the sensor system (e.g., supply chain facility 102 or storefront facility 104). These images and/or videos may include images or frames that include a label of a product or packaging or an individual (e.g., individual 120) within an environment of the sensor system 300. The vision capturing devices 302 may be any type of imaging device, camera, or vision sensor that is capable of collecting visual information. The vision capturing devices 302 may provide the visual information to the sensor system computing device 306, which may then process the visual information (e.g., with assistance of the processor 308). The vision capturing devices 302 may include a processor (e.g., a processor within the vision capturing devices 302 and separate from the processor 308) that is configured to obtain, generate, and/or provide the visual information to the device 306.

The olfactory sensor 304 receives olfactory information from the environment surrounding the sensor system 300. For example, the olfactory sensor 304 may be any type of device that detects and/or senses olfactory information from the environment surrounding the sensor system 300. For instance, the olfactory sensor 304 may be and/or include a single sensor with sensors replicating a specific olfactory receptor or receptors, or an array of sensors working together. For example, the olfactory sensor 304 may use an electronic sensor array, preprocessor, and a pattern recognition step to detect the smells from the sample of the pharmaceutical drug. The olfactory sensor 304 (e.g., an electronic nose including various types of sensors, such as metal oxides, electrochemical sensors, surface acoustic waves, quartz crystal microbalances, organic dyes, colorimetric sensors, conductive polymers, and mass spectrometers) is an electronic sensing device configured to detect odors or flavors. The expression "electronic sensing" refers to the capability of reproducing human senses using sensor arrays and pattern recognition systems. The stages or components of the olfactory sensor 304 for recognizing the smells may be similar to human olfaction and are performed for identification, comparison, quantification, and/or other applications, including data storage and retrieval. Some such devices are used for industrial purposes.

In operation, the olfactory sensor 304 may be configured to detect smells from the product or packaging of the product. Then, similar to the vision capturing devices 302, the olfactory sensor 304 may include a processor (e.g., a processor within the olfactory sensor 304 and separate from the processor 308) that is configured to obtain, generate, and/or provide the olfactory output data. The olfactory output data (e.g., the training information and/or drug expiration information) may indicate, be, and/or include one or more graphical representations of signals (e.g., electrical signals such as voltage measurements or readings) over a period of time (e.g., in seconds(s)). For instance, the graphical representation may be an electrical signal (e.g., voltage measurements) over two minutes, and each unique smell (e.g., each sample) may have a unique electrical signal. In some instances, the processor of the olfactory sensor 304 may use a short term Fourier transform (STFT) to determine the olfactory output data and/or generate the graphical representation. For instance, the olfactory sensor 304 may obtain time wave data, and the processor may use STFT to transform the obtained time wave data into the olfactory output data (e.g., the graphical representation). Additionally, and/or alternatively, the olfactory sensor 304 may provide the olfactory information to the sensor system computing device 306, which may then process the scent information (e.g., with assistance of the processor 308). In some instances, the olfactory information may be used to detect product conditions of the products.

While only the vision capturing devices 302 and the olfactory sensors 304 are shown in FIG. 3, in some examples, the sensor system 300 may include additional sensors such as a humidity sensor and/or a temperature sensor. For example, the humidity sensor may detect and measure water vapor including the humidity/moisture of the environment surrounding the sensor system 300. For instance, when a product or an individual 120 passes by the sensor system 300, the humidity sensor may detect information indicating the humidity/moisture of the individual 120 and provide it to the sensor system computing device 306. The sensor system processor 308 may use this information to determine whether the individual 120 is sweating and/or perspiring (e.g., whether the individual 120 may have a cold sweat or other health condition), or if the product is exposed to a humidity outside of an optimal range.

The temperature sensor may receive information indicating temperatures of an environment surrounding the sensor system 300. These temperatures may include a temperature of an individual, a product, or a portion of the environment where a product is stored within the vicinity of the sensor system 300. The temperature sensor may be any type of sensor that is capable of detecting temperatures of the surrounding environment and may be/include one or more infrared (IR) temperature sensors, thermistors, thermal cameras, and/or resistance temperature detectors (RTDs). For instance, the temperature sensor may detect temperature information that includes temperature(s) associated with the individual 120 and/or product and provide the temperature information to the sensor system computing device processor 308.

The sensor system computing device may include a processor 308. The processor 308 may be any type of hardware and/or software logic, such as a central processing unit (CPU), RASPBERRY PI processor/logic, controller, and/or logic, that executes computer executable instructions for performing the functions, processes, and/or methods described herein. For example, the processor 308 receives sensor information. For instance, the processor 308 may receive sensor information of one or more sensors (e.g., the vision capturing device 302, the olfactory sensor 304, the humidity sensor, and/or the temperature sensor) from the sensor system computing device 306. The processor 308 obtains (e.g., receives and/or retrieves) one or more ML-AI models (e.g., trained pharmaceutical ML-AI models 312, trained vision ML-AI models 314, and/or trained olfactory ML-AI models 316) from memory 310 and uses the ML-AI models to determine condition information of one or more products. For example, the processor 308 may input representations of the sensor information into the machine learning models to determine the condition information of a label of a product. The condition information may indicate the conditions that the product has been exposed to. For example, the condition information may indicate whether the product has been exposed to conditions (e.g., heat, humidity, light intensity) that are outside of an optimal range for the product.

Additionally, and/or alternatively, in some variations, the processor 308 may be used to determine the status of a variable ink of a label and/or the status of the product associated with label. For example, the processor 308 may use the condition information determined by one of the models 312, 314, 316, and, optionally, may additionally utilize known properties of the associated product, to determine whether the product has experienced non-optimal conditions (e.g., has been exposed to sub-optimal temperatures, sunlight, and/or other conditions that are described below). In other words, the processor 308 may use the outputs of the models 312, 314, and/or 316 to generate an indicator of the status of the product label. For instance, the indicator may be a flag associated with the item in an inventory system, an alert that an item should be checked to confirm a products condition, and/or an indication of an action to be taken (e.g., dispose of or discount the product).

The sensor system computing device 306 includes memory 310. The memory 310 may include the machine learning models (e.g., pharmaceutical ML-AI models 312, trained vision ML-AI models 314, and/or, when present, trained olfactory ML-AI models 316) that are used to determine a condition of a product label (e.g., label 606 shown in FIG. 6) as described above and in further detail below. These models may be stored and maintained in memory 310 and/or updated or stored in memory after being retrieved and/or received from the enterprise computing system 108. In some examples, the memory 310 may be and/or include a computer-usable or computer-readable medium such as, but not limited to, an electronic, magnetic, optical, electromagnetic, infrared, or semiconductor computer-readable medium. More specific examples (e.g., a non-exhaustive list) of the computer-readable medium may include the following: an electrical connection having one or more wires; a tangible medium such as a portable computer diskette, a hard disk, a time-dependent access memory (RAM such as the RAM 208), a ROM such as ROM 206, an erasable programmable read-only memory (EPROM or Flash memory), a compact disc read-only memory (CD_ROM), or other tangible optical or magnetic storage device. The computer-readable medium may store computer-readable instructions/program code for carrying out aspects of the present application. For example, when executed by the processor 308, the computer-readable instructions/program code may carry out operations of the present application including determining product conditions of a product using machine learning.

The sensor system 300 also includes a network interface 318. The processor 308 uses the network interface 318 to communicate with other devices and/or systems within the environment 100. The network interface 318 may include the functionalities and/or be the network interface 212 shown in FIG. 2. The processor 308 may communicate with the enterprise computing system 108, the user device 114, or the computing devices within the storefront facility 104 and/or supply chain facility 102 using the network interface 318. For example, the network interface 318 may provide an indicator and/or information indicating the condition of a label of a product, the product itself, or of the user 120 to the enterprise computing system 108. For instance, the processor 308 may determine that a product label (e.g., product label 606) has been exposed to conditions outside of an optimal range. The processor 308 may provide instructions to the user device 114 or the computing devices within the storefront facility 104 or supply chain facility 102 using the network interface 318 to check the products associated with the product label or the individual, or to take actions in response to the determined experienced conditions, e.g., remove the products from stock.

Additionally, and/or alternatively, the network interface 318 may communicate to other devices within the same physical location (e.g., storefront) as the sensor system 300. For example, the processor 308 may provide an alert indicating the condition of the product or product label to the other device within the storefront facility 104 (e.g., user device 114). An employee of the storefront facility 104 may view the alert and take action with respect to the associated products.

In some examples, by using the sensor system 300, the enterprise organization (e.g., via user device 114 and/or individual 120) may monitor the condition of products throughout an entire supply chain while reducing battery or power demands. For example, the sensing system may flag a product label associated with a product (e.g., by affixing a product label 606 to the product, product packaging, and/or to a pallet of the product or another structure that experiences the same or similar conditions to the product) for exhibiting a status of a variable ink that is associated with various experienced conditions. The enterprise organization might not be aware of all the conditions experienced by the product (e.g., if other parties participate in the supply chain of the product), but may take appropriate action with respect to the product due to the information of experienced conditions provided by the variable ink's response to various conditions. Furthermore, the user 120 of the enterprise organization may be aware of the product's condition and take appropriate action as well. As such, safe, sustainable, and effective management of inventory may be provided.

In some variations, the sensor system 300 is located within the supply chain facility 102 and/or the storefront facility 104. For example, the enterprise organization may install the sensor system 300 within the supply chain facility 102 or storefront facility 104. Additionally, and/or alternatively, the enterprise organization may update existing visual and olfactory systems to make data and/or information available to the remainder of sensor system 300, thereby forming a sensor system 300. The sensor system 300 may use the sensor information to determine the condition information indicating a status of the product label (e.g., whether the product label has experienced non-optimal conditions of the associated product) and provide a notification of this to the enterprise organization (e.g., user device 114 and/or the enterprise computing system 108). Accordingly, the enterprise organization may use the sensor system 300 as a monitoring device to determine whether/when action should be taken with respect to the products. As such, the enterprise organization may improve pharmaceutical or retail safety by avoiding the sale of products that have experienced non-optimal conditions.

FIG. 4 is an exemplary process 400 for using a sensing system to determine the status of a product label in accordance with one or more examples of the present application. The process 400 may be performed by a sensor system such as a sensing system comprising the olfactory system and/or vision system (e.g., the first olfactory system 116, the second olfactory system 118, the first vision system 110, and/or the second vision system 112 of FIG. 1). In some instances, the sensing system that is used to perform process 400 may be the sensor system 300 as shown in FIG. 3. In some examples, the sensing system may be and/or include the first and/or second vision system 110, 112, and/or first and/or second olfactory system 116, 118. For instance, the sensor system 300 and/or first/second vision system 110, 112 may obtain (e.g., retrieve, receive) the one or more first vision ML-AI models associated with a product from the enterprise computing system 108. Furthermore, it will be understood that any of the following blocks may be performed in any suitable order. The descriptions, illustrations, and processes of FIG. 4 are merely exemplary and the process 400 may use other descriptions, illustrations, and processes to determine the status of a product label.

For example, a sensing system may be deployed and/or installed within a part of a supply chain (e.g., a facility such as a warehouse or inventory of supply chain facility 102 or storefront facility 104, and additionally and/or alternatively, within a shipping container). The sensing system may capture data related to the characteristics of products, their packaging, and/or their product labels, and use ML-AI models with that data to determine whether the characteristics have changed over time (e.g., during shipping or while in the warehouse). By determining whether the characteristics have changed, the sensing system may also determine that the product has experienced conditions (e.g., environmental conditions) that the product, packaging, and/or product label is sensitive to. For example, by applying these variable inks to a product label, the inks may respond according to the conditions experienced by the product (e.g., amount of light exposure or humidity levels). The sensing system and variable ink may then track the conditions of the product with ink and packaging that is effectively an analog product label, rather than relying on electronically powered IoT devices alone. The sensing system may also alert a user (e.g., user 120) or inventory system that a product is flagged as improper, or is flagged for review and may need to be reviewed to assess the viability of the product and determine a course of action with respect to the product. Further, once a product has been flagged for review or as improper (e.g., because it has not been stored properly), a message may be sent to a backend server (e.g., enterprise computing system 108) to determine if this product was with other similarly susceptible products. If so, then those other similarly susceptible products may also be flagged for review or as improper. The sensing system may therefore provide for effective and efficient condition determination and management of products, thereby reducing an enterprise organization's environmental footprint and furthering the enterprise organization's environmental goals, such as furthering the pillars of the environmental, social, and corporate governance (ESG) criteria.

Figure 6:
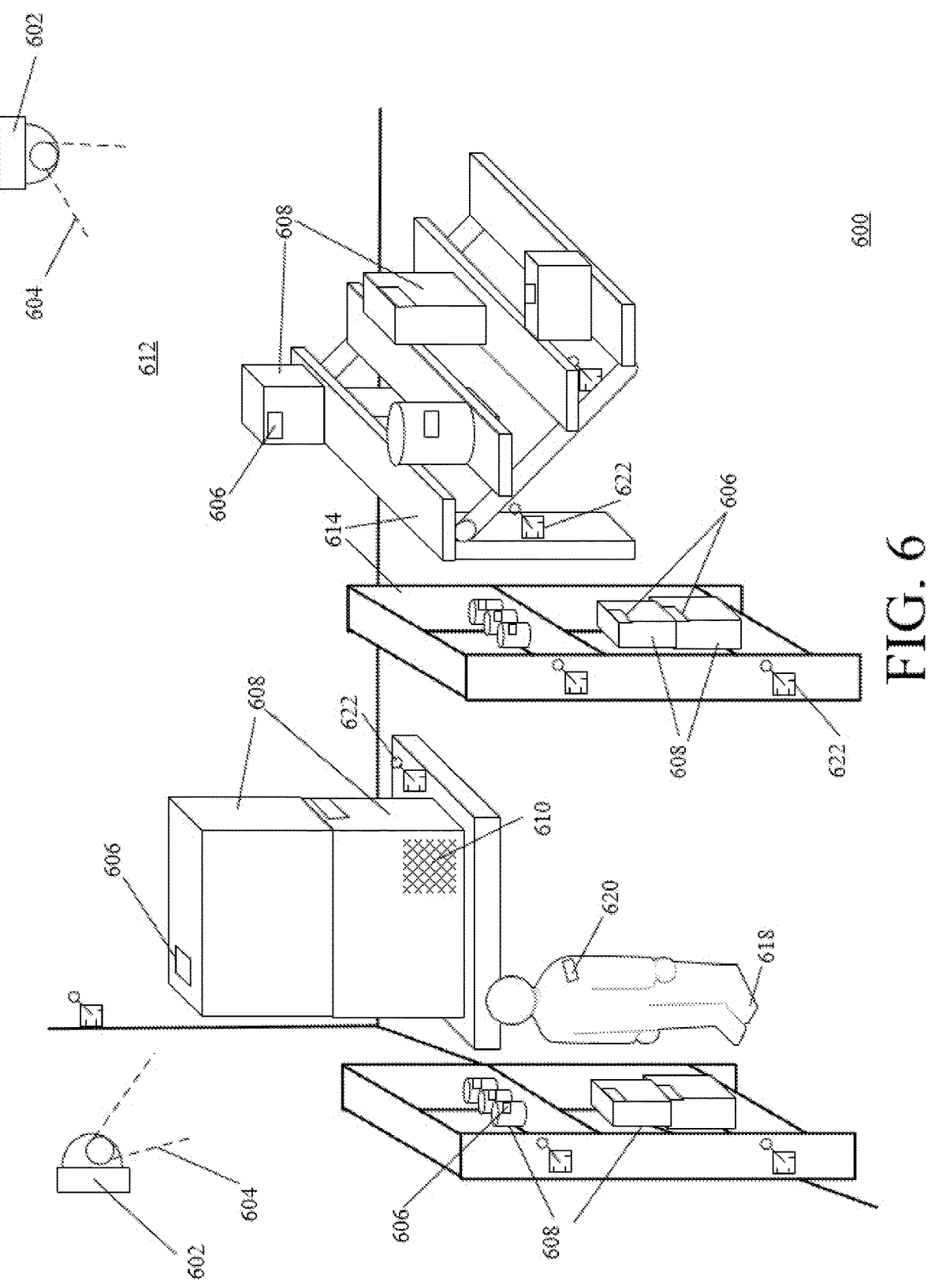
FIG. 6 is a depiction of an exemplary sensing system deployed in the exemplary environment in accordance with one or more examples of the present application.

For instance, FIG. 6 is a depiction of an exemplary sensing system deployed in the exemplary environment in accordance with one or more examples of the present application, and will be used to describe FIG. 4. For example, referring to FIG. 6, vision capturing devices (e.g., vision devices 602) of a sensing system are positioned within environment 600. The environment 600 may be within a facility of the environment 100 (e.g., supply chain facility 102 or storefront facility 104). Accordingly, in the example of the supply chain facility 102, the vision devices 602 may operate within the supply chain facility 102, and the vision devices 602 may be installed on structures of the facility 102 such as walls 612, ceilings, or storage racks 614, and/or on non-stationary elements such as robotics 616 (e.g., flying drones as in FIG. 8), robotics, and/or manually operated machinery such as forklifts. The vision device 602 may have a field of view 604 within which a product label 606 of a product 608 or a human label 620 of an individual 618, is visible by the vision device 602. The vision device 602 may then obtain an image of the entire field of view 604 containing the label 606 and/or 620, one or more labels 606 and/or 620, or an image of less than the entire field of view 604 but still containing at least a portion of the label 606 or 620.

At block 402, the sensing system (e.g., the first and/or second vision system 110, 112 and/or the sensor system 300) obtains (e.g., accesses) one or more first vision ML-AI models associated with a product. For instance, the product (e.g., product 608) may move through the supply chain or the manufacturing facility and may encounter one or more environmental conditions. For example, the product 608 may have a product label 606 affixed to or associated with the product 608 or packaging of the product, and that product label may have a variable ink that changes characteristics based on conditions corresponding to each type of variable ink. The sensing system may obtain one or more models trained to determine that the variable ink has changed characteristics.

Figure 7:
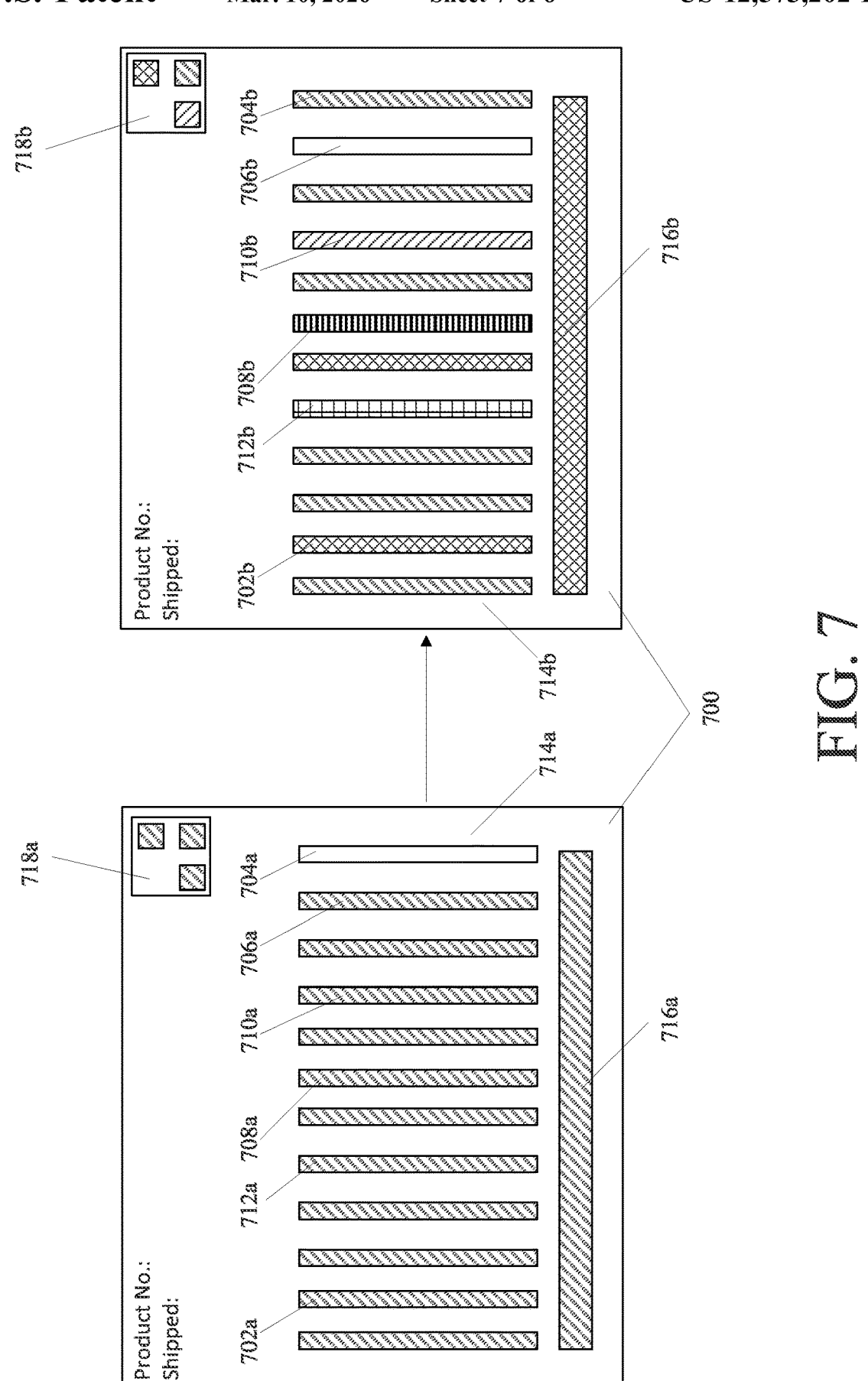
FIG. 7 shows an exemplary product label including variable ink in accordance with one or more examples of the present application.

In some instances, the product label (e.g., product label 606 or human label 620) imaged by the vision device 602 may be or include a variable ink label including one or more variable ink sections. FIG. 7 shows an exemplary product label 700 including variable ink in accordance with one or more examples of the present application. For instance, now referring to FIG. 7, the product label 700 may include variable ink sections (e.g., sections 702a and 702b) that are affixed to the product or associated with product such that the label and the product experience the same conditions. Each variable ink section may have a corresponding condition that, when experienced, causes the variable ink section to change from a base state to a corresponding changed state (e.g., environmental or electrical current conditions either within or outside of a range). One or more ML-AI vision models (e.g., model 312, 314) may be obtained that may determine whether the change from the variable ink section's base state to the corresponding state has occurred. The product label 700 that includes multiple different variable ink sections are merely exemplary, and in some instances, the product label 700 may include only a single variable ink section (e.g., a variable ink section that changes color based on a certain characteristic such as temperature).

The sensing system may also obtain one or more ML-AI vision models (e.g., based on a determined or expected variable ink or a determined or expected product). For example, the sensing system may obtain one or more ML-AI vision models, which may be associated with one or more particular types of variable ink such as a thermochromatic ink. Thermochromatic ink may be a type of ink or dye that changes color when temperatures increase and/or decrease. Additionally, and/or alternatively, the sensing system may determine the type of variable ink that is used by the product labels, and obtain ML-AI models based on the determined type. For instance, if the sensing system determines that the type of variable ink is a thermochromatic ink, the sensing system may obtain one or more thermochromatic ML-AI models from the one or more vision ML-AI models 314. Similarly, if the sensing system has determined that the product is a particular product (e.g., a pharmaceutical product), or is expecting/attempting to determine the conditions of a pharmaceutical product, one or more pharmaceutical ML-AI models 312 may be obtained from the one or more vision ML-AI models. Additionally, and/or alternatively, other product specific ML-AI models (e.g., food or sanitary products) may be similarly obtained by the sensing system. In some instances, for example, the sensing system may determine, based on the one or more images, whether or that a product is a pharmaceutical product 608 (e.g., medication) or a retail product 608. The sensing system may then determine condition information of the product 608 based on whether the product is the retail item or the pharmaceutical medication.

In some examples, the sensing system may obtain the ML-AI models (e.g., models 312, 314, and/or 316) after the ML-AI models are trained. For instance, the sensing system may obtain the ML-AI models after the models have been trained by the sensing system itself, or by the computing devices of supply chain facility 102, enterprise computing system 108, and/or storefront facility 104. In some examples, the enterprise computing system 108 has access to training data for one or more ML-AI models and may train the ML-AI models using this training data. In some examples, the enterprise computing system 108 shares the training of the ML-AI models (e.g., trains in parallel) with other computing devices (e.g., user device 114, storefront facility 104, and/or supply chain facility 102). For example, the enterprise computing system 108, user device 114, storefront facility 104, and/or supply chain facility 102 may individually or collectively have access to and/or maintain training data for the ML-AI models, and enterprise computing system 108 may train the ML-AI models using the local training data and/or the training data of the other computing devices. Additionally, and/or alternatively, the enterprise computing system 108 may perform training of the ML-AI models independently, or in combination with the user device 114, storefront facility 104, and/or supply chain facility 102. The sensing system may then obtain the trained ML-AI models from the enterprise computing system 108. The training of the ML-AI models is described in further detail below.

Additionally and/or alternatively, the sensing system may obtain the ML-AI models (e.g., models 312, 314, and/or 316) before the ML-AI models are trained. For example, vision systems 110, 112 may obtain ML-AI models 312, 314 and training data from the enterprise computing system 108, user device 114, storefront facility 104, and/or supply chain facility 102. The vision systems 110, 112 may then train the ML-AI models using the obtained training data, or may provide the untrained ML-AI models to the enterprise computing system 108, user device 114, storefront facility 104, and/or supply chain facility 102 for training.

In some instances, the sensing system is the sensing system 300. For example, referring to FIG. 3 and as described above, memory 310 may include trained pharmaceutical ML-AI models 312 and/or trained vision ML-AI models 314. The processor 308 may retrieve one or more of these models 312 and/or 314 from memory 310. The processor 308 may retrieve one or more of the models 312, 314 directly from memory 310 on the local device, a memory 310 on a second device (e.g., of the enterprise computing system 108), and/or the processor 308 may request the models 312 and/or 314 using network interface 318 from a second sensor system computing device 306 which maintains and/or stores that the models 312 and/or 314 in a memory 310.

In other words, the sensor system computing device/platform 306 may be a single device located within one facility, such as the supply chain facility 102, or the device 306 may be distributed across multiple locations, such as the storefront facility 104 and the enterprise computing system 108. If the device/platform 306 operates using a single device, the processor 308 may be within the same device 306 as the memory 310, and the processor may retrieve the models 312 and/or 314 from local memory 310. If the device/platform 306 is operating using local computing resources such as the processor 308 located at the storefront facility 104, and storing and/or maintains models 312 and/or 314 in a memory 310 at a second location in a back-end server 108, the processor 308 obtain the models 312 and/or 314 from the back-end server 108 via network 106. Additionally, and/or alternatively, one or more of the models 312 or 314 may be stored in a local memory 310, while the other models of models 312 or 314 are stored by the back-end server 108. In this instance, processor 308 may obtain either models 312 and/or 314 both from local memory 310 and from memory 310 of a second location (e.g., back-end server 108 or supply chain facility 102).

Additionally, and/or alternatively, the device 306 obtains one or more first olfactory ML-AI models 316 associated with a product. As described above with respect to models 312 and/or 314, one or more models 316 may be stored in local memory of sensing system (e.g., memory 310) and/or in a second memory in a second location (e.g., enterprise computing system/back-end server 108). Also as described above with respect to models 312 and/or 314, the sensing system (e.g., when the sensor system 300 is the sensing system, using processor 308) may retrieve the one or more models 316 from local memory (e.g., memory 310), from a second location (e.g., back-end server 108, user device 114, storefront facility 104, and/or supply chain facility 102), or from a combination of local memory and a second memory. Also as described above with respect to models 312 and 314, model 316 may be obtained by the sensing system in the trained or untrained state.

The sensing system may also obtain one or more ML-AI olfactory models 316 based on a determined or expected product. For example, if the sensing system has determined that the product is a fruit food product, or is expecting/attempting to determine the conditions of a fruit food product, the sensing system may obtain one or more fruit food ML-AI models from the one or more olfactory ML-AI models 316. Additionally, and/or alternatively, other product specific ML-AI models (e.g., food or sanitary products) may be similarly obtained by the sensing system.

At block 404, the sensing system obtains one or more images of a product label of the product, wherein the product label indicates a variable ink that changes colors based on environmental aspects. For example, as mentioned previously, a product (e.g., a retail product such as a food product and/or a pharmaceutical product such as a particular type of medication) may move through a supply chain from a manufacturer to a supply chain facility 102 (e.g., a DC) and/or a storefront facility 104 (e.g., a retail storefront). During the transportation from the manufacturer to the ultimate destination (e.g., retail storefront), the product may encounter multiple different environmental conditions. For instance, the product may need to be refrigerated to ensure its quality (e.g., the product may be a frozen or refrigerated product). Additionally, and/or alternatively, the product may deteriorate in quality if exposed to sunlight. The product label (e.g., product label 700) may include a type of variable ink (e.g., thermochromatic and/or photochromic) that changes characteristics (e.g., color) based on encountering certain environmental conditions during transport from the manufacturer to the storefront facility 104. For instance, the variable ink on the product label may change colors based on being exposed to certain temperatures and/or exposed to sunlight. For example, during transportation from the manufacturer to the supply chain facility 102, the refrigerated product may have accidentally been left outside in an unrefrigerated environment for a certain amount of time. Based on encountering this environmental condition, the variable ink on the product label of the refrigerated product may change colors. The sensing system (e.g., at the supply chain facility 102 and/or the storefront facility 104) may obtain one or more images of the product label of the product (e.g., images of the color change based on the product encountering the environmental condition).

In some instances, the sensing system is the sensor system 300. When the sensing system is sensor system 300, vision capturing devices 302 may obtain images of a product label 606 and/or an individual 618 and provide the images and/or a representation of the images to the processor 308.

In some examples, the sensing system may be the first vision system 110 deployed in the supply chain facility 102, the second vision system 112 deployed in the storefront facility 104, or a cooperative combination of the first vision system 110 and the second vision system 112. In these examples, vision devices 602 of the first vision system 110 may obtain one or more images of a product label 606 in the supply chain facility, and/or vision devices 602 of the second vision system 112 may obtain one or more images of a product label 606 in the storefront facility 104.

Vision devices 602 may also be deployed in specific locations within the facilities 102 and 104. For example, referring to FIG. 8, a facility environment 800 (e.g., of supply-chain facility 102 or storefront facility 104) may include multiple different sections for performing different tasks and storing different products. For instance, environment 800 may include: an inventory section 801, which may be designated for specific types of food goods; an inventory section 802, which may be designated for pharmaceutical products; an inventory section 803, which may be designated for dry goods and humidity sensitive goods; an inventory section 804, which may be designated for light sensitive goods; an inventory section 805, which may be designated for temperature sensitive goods (e.g., cold storage); an inventory section 806, which may be designated for light response goods (e.g., goods with fluorescent packaging); an inventory section 807, which may be designated for static sensitive goods (e.g., goods with electrochromic packaging); a receiving bay 808, and a packaging zone 809. Vision devices 602 and olfactory sensors 622 may be deployed within one or more of these sections or within operational range of one or more of these sections. Vision devices 602 and olfactory sensor 622 may obtain images and olfactory information from products 608 within the respective sections, and/or from products 608 within operational range. The environment 800 may also include a processing center 816. The processing center 816 may receive images, recordings, and/or olfactory sensor information from vision devices 602 and olfactory sensor 622. The processing center 816 may then perform a number of functions for process 400. For example, the processing center 816 may receive images from vision devices 810, 812 and olfactory information from olfactory sensors 622, train and/or retrieve any of models 312, 314, and/or 316, process the received information into representations for use in one or more of the models 312, 314, and/or 316, execute one or more of the models 312, 314, and/or 316, output indicators of the status of a product 608 or product label 606, and/or run an inventory management system.

Vision devices 602 may be deployed with a field of view 604 including multiple sections, such as vision device 810, or deployed with a field of view 604 limited to certain sections or a single section, such as vision device 812. When deployed in view of multiple sections, fewer vision devices 602 may be required to image and/or record products 608. For example, vision device 810 may be deployed with a field of view including inventory section 803 and 802. The sensing system may then obtain images of product labels 606 associated with both pharmaceutical and dry goods products 608. The sensing system may then obtain one or more pharmaceutical ML-AI models 312 and a humidity sensitive product label model from the one or more vision ML-AI models 314, and execute both using the input provided by a single vision device 602.

When vision devices 602 are deployed in view of a limited number of section, vision devices 602 may utilize camera and/or sensor structures that allow them to pick up more sensitive information specific to the products in a section. For example, vision device 812 may be deployed with a field of view 604 including only inventory section 806, and may be deployed with a camera having a special sensitivity to light of a wavelength matching the wavelength given off by a fluorescent variable ink. The vision device 812 may image products 608 in inventory section 806. The sensing system, based on the vision device 812 operating with respect to a defined type of product 608, may obtain a fluorescent packaging specific model from the ML-AI models 314. The sensing system may then input the images obtained from the vision device 812 and/or representation of the image into the fluorescent packaging specific model and execute the model.

Additionally, and/or alternatively, when the vision devices 602 are deployed on non-stationary elements (e.g., flying drone 616), the one or more vision devices 818 may image product labels 606 associated with products 608 of multiple different types as the drone 616 moves the vision device 818 past multiple different types of inventory sections, and send the images and/or recordings to the processing center 816 in combination with other information (e.g., location information of the drone 616 at the time of the image). Similarly, olfactory sensors 622 may be deployed on non-stationary elements (e.g., flying drone 616), and may sense scents associated with products 608 of multiple different types as the drone 616 moves the olfactory sensor 622 past multiple different types of inventory sections, and send the olfactory information to the processing center 816 in combination with other information (e.g., location information of the drone 616 at the time of the olfactory information collection).

The sensing system may obtain one or more of these images from the vision devices. For example, the sensing system may be vision system 112, and may obtain the one or more images of the vision devices 602 in the supply chain facility 102 from the first vision system 110 and/or computing devices of the supply chain facility 102 via network 106. Additionally, and/or alternatively, the vision system 112 may include the vision devices 602 and obtain the images directly from vision devices 602 and/or computing devices of the storefront facility 104.

Now referring to FIG. 7, the label 606 or 620 imaged by the vision device 602 may be or include a variable ink label 700 including one or more variable ink sections. The variable ink sections may change from a base state to a corresponding changed state upon experiencing respective conditions and/or aspects of the environment (e.g., environmental conditions, electrical current conditions). These changes from a base state to a corresponding state may also be in response to conditions either within or outside of a range (temperature range, humidity levels, and/or amount of light exposure), or in response to a specific condition of the ink section (e.g., when hydrochromic ink contacts water and/or experiences rain/water damage, and/or when electrochromic ink experiences an applied electrical current to an electronic parcel or theft deterrent feature). The vision device 602 may then obtain one or more images of the product label 606 containing the variable ink section 700 in a base state and/or variable ink section in a corresponding changed state.

For example, the variable ink label 700 may include thermochromatic ink sections 702a and/or 702b that change color in response to different temperatures. The thermochromatic ink sections 702a, upon experiencing a temperature above a threshold temperature, may change color and exhibit the changed state of the ink section 702b. The change in color may be binary in nature (e.g., blue in a base state and red in a changed state) or spectrum based (e.g., red in a completely base state, green in a changed state, and the color of the ink section 702b is more green the more exposed the ink section 702b is). The change in color from ink section 702a to 702b may also be a change in tint (e.g., a base state is yellow and the changed state increases in darkness proportionally to the degree of exposure). The vision device 606 may obtain one or more images of the product label 606 including thermochromatic ink sections 702a and/or one or more images of the product label 606 including thermochromatic ink sections 702b.

Additionally, and/or alternatively, the variable ink label 700 may include fluorescing ink sections 704a and/or 704b. The fluorescing ink section 704a, upon absorbing ultraviolet (UV) light, may re-emit the UV light within a visible spectrum, thereby changing color and exhibiting the changed state of the ink section 704b. The vision device 606 may obtain one or more images of the product label 606 including fluorescing ink section 704a and/or one or more images of the product label 606 including fluorescing ink section 704b. The one or more images of the product label 606 may be used to identify whether or that products 608 are authentic. The one or more images may also be used to identify with an analog identifier instead of bar codes, QR codes, and the like.

Additionally, and/or alternatively, the variable ink label 700 may include glow-in-the-dark (GID) ink sections 706a and/or 706b that absorb light and re-emit that light (e.g., glow). The GID ink section 706a, upon absorbing light, may re-emit the light over time (e.g., glowing when environment 606 is less luminous than GID ink section 706b), thereby changing luminescence, brightness, intensity, and/or color and exhibiting the changed state of the ink section 706b. The vision device 606 may obtain one or more images of the product label 606 including GID ink section 706a and/or one or more images of the product label 606 including GID ink section 706b. The one or more images may include a time lapse or time-to-live type of ink. As the luminescence fades, the determined condition information may determine the life left of a product 608 as it approaches the expiration date of product 608 based on the life left of the GID ink section 706*b*.

Additionally, and/or alternatively, the variable ink label 700 may include photochromic ink sections 708*a* and/or 708*b* that activate when light is incident upon them. The photochromic ink section 708*a*, upon being exposed to sunlight and/or temperatures outside of an optimal range, may change color and exhibit the changed state of the ink section 708*b*. The vision device 606 may obtain one or more images of the product label 606 including photochromic ink section 708*a* and/or one or more images of the product label 606 including photochromic ink section 708*b*. The one or more images may be used to make sure products 608 associated with product labels 606 that may need to be kept in the dark are accurately done so, thereby extending the life of product 608.

Additionally, and/or alternatively, the variable ink label 700 may include electrochromic ink sections 710*a* and/or 710*b*. The electrochromic ink section 710*a*, upon being exposed to an electrical current or electrical potentials above a certain voltage, may change color and exhibit the changed state of the ink section 710*b*. The vision device 606 may obtain one or more images the product label 606 including electrochromic ink section 710*a* and/or one or more images of the product label 606 including electrochromic ink section 710*b*.

Additionally, and/or alternatively, the variable ink label 700 may include piezochromic ink sections 712*a* and/or 712*b*. The piezochromic ink section 712*a*, upon application of force or pressure above a threshold (e.g., pressurized atmospheres, shock, impact, or stretching) may change color and exhibit the changed state of the ink section 712*b*. The vision device 606 may obtain one or more images the product label 606 including piezochromic ink section 712*a* and/or one or more images of the product label 606 including piezochromic ink section 712*b*. The one or more images may help determine whether or that a product 608 associated with product label 606 went through high pressure testing, helping ensure that the product 608 has met certain standards for sale.

Additionally, and/or alternatively, the variable ink sections of the variable ink label 700 of FIG. 7 may also be an independent section of the product label 606. For instance, a product label 606 may include a strip 716*a* of a variable ink label 700. This strip 716*a*, upon experiencing appropriate changing conditions, may change state to strip 716*b*. Vision devices 602 may then obtain one or more images of the strip 716*a* and/or strip 716*b*, and based on the change from strip 716*a* to 716*b* or the state of strip 716*a* or 716*b*, a status of the variable ink may be determined. Additionally, and/or alternatively, variable ink sections may be imbedded into the packaging of the product and/or integrated into a standard barcode format (e.g., universal product code (UPC) bar code 714*a*, quick response (QR) code 718*a*, AZTEC code) such that upon the variable ink section changing from a first, base state to a second, changed state, a reading of the bar code 714*a* or QR code 718*a* is affected. For example, the bar code 714*a* or QR code 718*a*, when imaged, may be processed by a respective pharmaceutical model 312 or vision model 314 to output a first identification or determination. However, the bar code 712*a* or QR code 718*a*, when processed by the same respective pharmaceutical model 312 or vision model 314, may cause an output of a second identification or determination. For instance, a pharmaceutical model 312 may process the bar code 712*a* and/or QR code 718*a* to output a first determination, such as "acetaminophen." The same pharmaceutical model 312 may process the bar code 712*b* and/or QR code 718*b* to output the determination "acetaminophen-risk."

Additionally, and/or alternatively, the sensing system may include one or more olfactory sensors 622 that obtain olfactory information indicating a scent of the product. The olfactory sensors 622 are positioned within environment 600. Accordingly, as in FIGS. 6 and 8, the olfactory sensor 622 may operate within the supply chain facility 102, and the olfactory sensor 622 may be installed on structures of the facility 102 intended to be at least momentarily within proximity (e.g., 2 feet, 2 meters) or positioned within a scent trail (e.g., in an air exhaust) to products 622 and/or individual 618, such as walls 612, ceilings, or storage racks 614, and/or on non-stationary elements such as flying drones 616, robotics, and/or manually operated machinery such as forklifts. When mounted to non-stationary elements such as flying drones 616, a single olfactory sensor 622 may quickly collect olfactory information from a multitude of products 608. When mounted to stationary elements such as walls of facilities 102 and/or 104, the olfactory sensor 622 may be specialized to correspond with a type of product 608 that is intended to be positioned next to that part of the wall of the facility 102 or 104. For example, as in FIG. 8, an olfactory sensor 622 deployed in inventory area 805 could be optimized by including sensing components specific to cold storage goods, and/or the collected data could be used as an input to a delegated cold storage goods olfactory ML-AI model from the one or more olfactory ML-AI models 316.

In some instances, the product label 606 associated with the product 608, packaging 610 of the product 608, and/or product 608 may provide olfactory information. For example, a scented ink may be applied to product label 606 or packaging 610, or product 608 may inherently emit a scent. Humidity in the air may trap odor causing molecules and cause them to not only travel farther, but also linger longer, resulting in a noticeable bad smell, allowing for olfactory sensors 622 to provide olfactory information related to the humidity of the environmental conditions experienced by product label 606, packaging 610, and/or product 608. Similarly, light may change scent volatiles (e.g., in plants and fruits) and scent may be affected by the temperature of the environment. As a result, olfactory information obtained by olfactory sensors 622 may be used to determine condition information based on temperature changes, light changes, and humidity changes, that product label 606, packaging 610, and/or product 608 may have experienced.

The olfactory sensor 622 may be positioned such that a scent of a product 608, an olfactory packaging 610 of a product 608, or an individual 618 may be sensed by the olfactory sensor 622. The olfactory sensor 622 may then obtain olfactory information indicating a scent of the product 608, the olfactory packaging 610 of the product 608, or the individual 618. Because the scent emitted by the product 608, olfactory packaging 610 of the product 608, or the individual 618 may change in response to different conditions. Therefore, a different scent may be obtained by a first olfactory system 116 (e.g., a base scent) than by a second olfactory system 118 (e.g., a changed scent). For example, the base scent may correspond to a pharmaceutical product or food product that is stable. The changed scent may correspond to a pharmaceutical product or food product that is now unstable, and has changed in composition.

At block 406, the sensing system determines condition information indicating a status of the product label based on executing the one or more first vision ML-AI models and the one or more images of the product label indicating the status of the variable ink. For instance, after obtaining the one or more images of the product label (e.g., an image of the product label 700 indicating one or more types of variable ink), the sensing system may input a representation associated with the image (e.g., red, green, blue (RGB) color values and/or other information associated with the image) into the one or more first vision ML-AI models. For example, the sensing system may modify (e.g., crop) the image such that only the portion of the product label with the variable ink is shown. Then, the sensing system may input information associated with the modified image into the ML-AI models (e.g., the vision ML-AI models 314 and/or the pharmaceutical ML-AI models 312) to generate an output. The sensing system may use the output to determine the condition information indicating the status of the product label.

In some examples, the sensing system may be the vision system 110 and/or 112. The vision system 110 and/or 112 may input the images of the product label obtained in block 404 directly into the ML-AI models obtained at block 402, and the ML-AI models may determine the visual ML-AI information (e.g., condition information) that indicates a status of the product label (e.g., changed state, base state). The visual ML-AI information may be a first condition confidence value that is output from the one or more first vision ML-AI models providing a confidence value in the condition of the product label 606. Additionally, and/or alternatively, sensing system may obtain a representation of the images of the product label obtained in block 404 and input the representations to the one or more ML-AI models obtained at block 402 to determine the condition information that indicates a status of the product label (e.g., changed state, base state).

In some instances, the condition information includes features of the labels 606 and/or 620, which provide information on the environmental conditions or aspects that have been experienced (e.g., the color or characteristics of one or more variable ink sections). For example, the condition information may include the color or light emittance of a variable ink section (e.g., ink sections 702b, 704b). In some examples, the condition information indicates status of product label because the condition information is a visual or olfactory indicator of the status of the product label. For instance, if thermochromatic ink sections 702a have changed to thermochromatic ink sections 702b, the status of the product label is "exposed" as indicated by the condition information of the product label's 606 exhibited color of thermochromatic ink section 702b. The sensing system, by inputting an obtained image and/or representation of thermochromatic ink section 702b to a vision ML-AI model, and executing that model, may determine that because the product label 606 exhibits the color of thermochromatic ink section 702b, instead of thermochromatic ink section 702a, that the status of the product label 606 is "exposed." Similarly, the sensing system, by inputting an obtained image and/or representation to a vision ML-AI model, and executing that model, for the obtained image and/or representation of GID ink section 706b, may determine that because the product label 606 exhibits the brightness of GID ink section 706b, instead of GID ink section 706a, that status of the product label 606 is "base."

In other words, the sensing system may use the condition information from the obtained images as an input to an ML-AI model to determine whether or that the product label has been exposed corresponding conditions, and those conditions may be specifically identifiable based on how the variable ink section changes.

In some instances, the conditions that activate the ink (thereby affecting the status of the product label 606) correspond to the conditions that affect the status of the product 608. The sensing system may maintain information on conditions the product is susceptible to, and based on which variable ink strip of a plurality of variable ink strips of the product label 606 is in a changed state, such as thermochromatic ink strip 702b, determine if the product is susceptible to the conditions that activate the variable ink strip from strip 702a to 702b. When the sensing system determines that the product is susceptible to the condition that activate the variable ink strip from strip 702a to 702b (e.g., heat or humidity), the sensing system may determine that the product may have experienced these conditions as well, and should be checked.

Additionally, and/or alternatively, when the sensing system includes one or more olfactory sensors 622, the sensing system may determine olfactory ML-AI information indicating a status of the product based on executing the one or more olfactory ML-AI models and the one or more obtained scents. Similar to the use of visual ML-AI information, the olfactory information may include features of a detected scent that provide information on the environmental conditions or aspects that have been experienced (e.g., the changed scent). In some examples, the olfactory ML-AI information the olfactory ML-AI information is a second condition confidence value that is output from the one or more second olfactory ML-AI models that provides a confidence value in the condition of the product label 606, packaging 610, or product 608. Additionally, and/or alternatively, the olfactory ML-AI information indicates a status of product because the condition information is an olfactory indicator of the status of the product label. For instance, if the scent has changed from a base scent to a changed scent, the status of the product label is "exposed" as indicated by the condition information of the product 608's emitted scent. The sensing system, by inputting an obtained scent and/or representation of the scent to an olfactory ML-AI model, and executing that model, may determine that because the product 608 emits the scent of changed scent, instead of a base scent, that a status of the product 608 is "exposed."

Additionally, and/or alternatively, the sensing system may determine the condition information indicating the status of the product label based on both the output of the vision ML-AI model and the one or more images and/or representations and the output of the olfactory ML-AI models and the olfactory information. In other words, in some instances, the sensing system uses the olfactory systems (e.g., olfactory systems 116, 118) and the one or more olfactory ML-AI models (e.g., olfactory models 316) together to provide an indicator (e.g., the status). In some examples, determining the condition information indicating a status of the product label 606 includes determining the condition information utilizing a federated learning ML-AI approach and/or as a weighted average of the first condition confidence value of the visual ML-AI information and the second condition confidence value of the olfactory ML-AI information. For instance, the first and second confidence values output from the vision ML-AI model and the olfactory ML-AI model may indicate percentages (e.g., 96% or 93%) that the product was not exposed to certain environmental conditions that may deteriorate the condition of the product. The sensing system may determine a weighted average (e.g., 94.5%) based on the confidence values and compare the weighted average with one or more thresholds. For example, based on the comparison, the sensing system may determine the status of the product label/product (e.g., based on the weighted average being above a 90% threshold, the sensing system may determine the product was not exposed to certain environmental conditions).

At block 408, the sensing system outputs an indicator indicating the status of the product label based on the condition information. For example, when the sensing system is vision system 112, the vision system 112 may output the indicator to the user device 114, vision system 110, and/or the computing devices of enterprise computing system 108, storefront facility 104, and/or supply chain facility 102 via the network 106. In some instances, when the sensing system includes the sensor system 300, the indicator may be output using the network interface 318 to provide the indicator to network 106. In some examples, the sensing system is the vision system 110, and the vision system 110 may output the indicator to the user device 114, vision system 112, and/or the computing devices of enterprise computing system 108, storefront facility 104, and/or supply chain facility 102 via the network 106. In some example, the sensing system is a cooperative combination of the vision system 110 and the vision system 112, and the combination may output the indicator to the user device 114 and/or the computing devices of enterprise computing system 108, storefront facility 104, and/or supply chain facility 102 via the network 106.

The indicator may be an internal flagging. For example, the sensing system may output an indicator to a further computing device (e.g., enterprise computing service 108) that will result in registering the indicator in an inventory management system of the further computing device, and/or updating information on the product associated with the product label of process 400 (e.g., product 608). The sensing system may also alert a user 120 or inventory system that a product 608 is flagged as exposed, or is flagged for review and may need to be reviewed to assess the viability of the product and determine a course of action with respect to the product. Further, once the product 608 has been flagged for review or as exposed (e.g., because it is not in a ceiling or floor threshold for proper storage), a message may be sent to the further computing device (e.g., user device 114, backend server 108) to determine if this product was with other similarly susceptible products. If so, then those other similarly susceptible product(s) 606 may also be flagged for review or as exposed.

The sensing system may output the indicator based on the condition information determined at block 406. For example, the sensing system may determine at block 406 that the product label 606 is exposed. Based on determining that the product label 606 is exposed, the sensing system may output an indicator that the product label 606 is exposed to a user device 114 for the purpose of user 120 checking the product 608 associated with the product label 606.

In some examples, the sensing system provides to a user device 114 the indicator indicating the status of the product label based on the condition information, and the user device 114 receives the indicator indicating the status of the product label and causes display of a prompt indicating a condition of the product. For example, the user device 114 may receive the indicator that the product label 606 is exposed, and cause display of a prompt (e.g., push notification or new text within an application) that indicates the product 608 (being associated with the product label 606) is exposed. The prompt may further indicate a course of action for the user 120 to take. In some instances, the course of action may include checking the condition of product 608, removing product 608 from a retail section, disposing of product 608, discounting a sale price of product 608, and shortening, prolonging, or cancelling a shipping date of the product 608.

Additionally, and/or alternatively, the enterprise computing system 108 may perform process 400. For example, the enterprise computing system 108 may communicate over network 106 with a sensing system such as the first vision system 110 and/or second vision system 112 (alone or in combination), the first olfactory system 116 and/or second olfactory system 118 when present (alone or in combination), or a combination of vision systems 110, 112 and olfactory systems 116, 118. The enterprise computing system 108 may perform the processing and execution of the ML-AI models and receive images and/or representations of images, olfactory information, and/or models 312, 314, 316 over network 106 from the sensing system.

In some examples, at block 402, the enterprise computing system 108 obtains one or more first vision ML-AI models associated with a product. The enterprise computing system 108 may store the models 312, 314, and/or 316 in local memory, and/or may obtain one or more models 312, 314, 316 from user device 114, the computing devices of supply chain facility 102, and the computing devices of storefront facility 104.

In some instances, at block 404, the enterprise computing system 108 obtains one or more images of a product label of the product, wherein the product label indicates a variable ink that changes colors based on environmental aspects. For example, the enterprise computing system 108 may obtain (e.g., retrieve, receive), from the sensing system, one or more images of a product label 606 associated with a product 608 and/or an individual 618, where the one or more images are captured by vision devices 302 of the sensing system.

In some examples, at block 406, the enterprise computing system 108 determines condition information indicating a status of the product label based on executing the one or more first vision ML-AI models and the one or more images of the product label indicating the status of the variable ink. For example, the enterprise computing system 108 may input the images of the product label obtained from the sensing system in block 404 directly into the ML-AI models obtained at block 402, and the ML-AI models may determine the condition information that indicates a status of the product label (e.g., changed state, base state). To determine the condition information, the enterprise computing system 108 may execute the one or more obtained ML-AI models. Additionally, and/or alternatively, the enterprise computing system 108 may generate or obtain a representation of the images of the product label 606 obtained from the sensing system in block 404, and input the representations to the one or more ML-AI models obtained at block 402 to determine the condition information that indicates a status of the product label (e.g., changed state, base state).

In some examples, at block 408, the enterprise computing system 108 may output the indicator indicating the status of the product label based on the condition information. For example, the enterprise computing system 108 may output the indicator to the user device 114, vision systems 110, 112, olfactory system 116, 118 (when present), and/or the computing devices of storefront facility 104 and/or supply chain facility 102 via the network 106. In some instances, when the sensing system includes the sensor system 300, the indicator may be output using the network interface 318 to provide the indicator to network 106. In some examples, the sensing system is the vision system 110, and the vision system 110 may output the indicator to the user device 114, vision system 112, and/or the computing devices of enterprise computing system 108, storefront facility 104, and/or supply chain facility 102 via the network 106.

In some examples, process 400 may be performed with multiple components of environment 100 cooperating together. For instance, one or more vision capturing devices 602 of a vision system 110, 112 may obtain one or more images of a product label 606 of a product 608 (e.g., associated with product 608), and the product label 606 may indicate a variable ink that changes colors based on environmental aspects. Computing devices (e.g., processor 308 and/or memory 310) of a vision system 110, 112 (alternatively or together) may receive (e.g., via network interface 318 of sensor system 300), from enterprise computing system 108, one or more first (ML-AI) models associated with the product 608. The computing devices of the vision system 110, 112 may determine condition information indicating a status of the product label based on executing the one or more first ML-AI models and the one or more images of the product label indicating the variable ink. The computing devices of vision system 110, 112 may provide, to a user device 114, an indicator indicating the status of the product label based on the condition information. The user device 114 may receive the indicator indicating the status of the product label and cause display of a prompt (e.g., to individual 120) indicating a condition of the product 608.

FIG. 5 is an exemplary process 500 for using a sensing system to determine the status of a product label in accordance with one or more examples of the present application. The process 500 may be performed by a sensing system such as a sensing system comprising the olfactory system and/or vision system (e.g., the first olfactory system 116 and/or the first vision system 110 of FIG. 1). In some instances, the sensing system may be the sensor system 300 as shown in FIG. 3, such that the sensor system 300 may be used to perform process 500. In some examples, the sensing system may be the first and/or second vision system 110, 112, or first and/or second vision system 110, 112 which include sensor system 300. Furthermore, it will be understood that any of the following blocks may be performed in any suitable order. The descriptions, illustrations, and processes of FIG. 5 are merely exemplary and the process 500 may use other descriptions, illustrations, and processes to determine the status of a product label.

At block 502, the sensing system trains one or more first vision ML-AI models based on product label training information indicating statuses of a plurality of product label. For example, at block 502, the sensing system obtains training data that may indicate condition information indicating a status of the product label based on images of a product label's 606 variable ink. The sensing system may obtain a training dataset by obtaining one or more images of the variable ink in a base state (e.g., using vision system 110 in supply chain facility 102 and/or using a vision system at a manufacturing plant) and/or one or more images of the variable ink in a changed state (e.g., using vision system 112 in storefront facility 104). For instance, the sensing system may obtain images of the product label in a base state (e.g., prior to encountering any environmental conditions). For example, the sensing system may be situated at a manufacturing plant that manufactures the product (e.g., the prescription drug and/or the retail product). Prior to placing the product label onto the product (e.g., the product packaging), the sensing system may obtain images of the product label. Thus, the sensing system may train the vision ML-AI models based on the product label training information (e.g., the images of the product label at the base state).

The sensing system may use the training dataset to train the ML-AI models (e.g., models 312, 314, 316) to determine whether or that a product label 606 includes a variable ink section that has changed from a base state to a changed state. The change in state may indicate the status of the product label 606, and may indicate at what point during a supply chain the product label 606 was exposed to corresponding environmental conditions based on when the product label 606 was last determined to be in a base state and when the product label 608 was first determined to be in a changed state. In other words, the product label training information may include images of multiple different product labels, and at least one of the images may indicate (e.g., an image from facility 102) a baseline condition of a first product label 606 prior to being applied to any products 608. One or more first vision ML-AI models (e.g., models 312, 314), then, may include an unsupervised ML-AI model, supervised ML-AI model, and/or deep learning model.

Additionally, and/or alternatively, the sensing system may obtain a training dataset by obtaining one or more images of the variable ink section in a changed state (e.g., using vision system 110 in supply chain facility 102 or vision system 112 in storefront facility 104). The sensing system may use this training dataset to train the ML-AI models (e.g., models 312, 314, 316) to determine whether or that a product label 606 includes a variable ink section that is exhibiting a certain color, scent, or characteristic. The exhibited color, scent, or characteristic may be the result of the respective ink section's changed state, and therefore may be all that is needed to determine condition information indicating a status of the product label.

Additionally, and/or alternatively, the sensing system obtains training data based on the type of products. For instance, the one or more pharmaceutical ML-AI models 312 may include a first pharmaceutical ML-AI model associated with a first pharmaceutical product 608 and a second pharmaceutical ML-AI model associated with a second pharmaceutical product 608. The sensing system may obtain multiple images of one or more product labels 606 of the first pharmaceutical product 608 with a variable ink section at a first base state to obtain a first baseline dataset, and train the first pharmaceutical ML-AI model on the baseline dataset. The sensing system may obtain multiple images of one or more product labels 606 of the second pharmaceutical product 608 with a variable ink section at a second base state to obtain a second baseline dataset different from the first baseline dataset, and train the second pharmaceutical ML-AI model on the second baseline dataset.

For example, different pharmaceutical products may have different storage and/or transportation requirements. For instance, a first pharmaceutical product may be able to be stored at room temperature, but not exposed to sunlight. A second pharmaceutical product may be able to be exposed to sunlight, but may need to be stored in a refrigerated environment. Additionally, and/or alternatively, a third pharmaceutical product may need to be stored at an even lower temperature than the second pharmaceutical product. Given these different requirements, the sensing system may train different ML-AI models for the different pharmaceutical products. For instance, each ML-AI model may be trained and/or used for a particular type of pharmaceutical product (e.g., a first, second, and third ML-AI model for the first, second, third pharmaceutical product). Additionally, and/or alternatively, the retail items may also have different ML-AI models (e.g., a first ML-AI model for a first retail item such as a retail item that needs to be refrigerated, and a second ML-AI model for a second retail item such as a retail item that needs to be frozen).

Additionally, and/or alternatively, enterprise computing system 108 may train the one or more ML-AI models. For example, enterprise computing system 108 may obtain images, representations, and/or a training dataset for the ML-AI models from the sensing system (e.g. vision system 110, 112), may generate representations and/or a training dataset for the ML-AI models (e.g., models 312, 314, 316) based on the obtained images, and may obtain the ML-AI models from local memory or from a non-local memory via network 106. The enterprise computing system 108 may then train the ML-AI models on the representations and/or training dataset. Additionally, and/or alternatively, the enterprise computing system 108 may train the one or more ML-AI models, and the sensing system may obtain (e.g., receive) the one or more trained ML-AI models from the enterprise computing system 108 in order to execute the one or more trained ML-AI models.

At block 504, the sensing system stores the trained one or more first vision ML-AI models in memory. For instance, when the sensing system is the vision system 110, the vision system 110 may store the one or more vision ML-AI models trained at block 502 in a local memory of the supply chain facility 102 (e.g., memory 310 when the vision system 110 includes the structure of sensor system 300), and/or in a memory of the user device 114, enterprise computing system 108, and/or computing devices of storefront facility 104 via network 106. When the sensing system is the vision system 112, the vision system 112 may store the one or more vision ML-AI models trained at block 502 in a local memory of the storefront facility 104 (e.g., memory 310 when the vision system 110 includes the structure of sensor system 300), and/or in a memory of the user device 114, enterprise computing system 108, and/or computing devices of supply chain facility 102 via network 106. The vision systems 110, 112 may have trained the ML-AI models at block 502, or may obtain the trained ML-AI models from the enterprise computing system 108 or user device 114 that performed training at 502 for storing the ML-AI models in memory.

Additionally, and/or alternatively, the enterprise computing system 108 may store the vision ML-AI models trained at block 502 in a local memory of the enterprise computing facility 108, and/or in a memory of the user device 114, computing devices of supply chain facility 102, and/or the computing devices of the storefront facility 104 via network 106. The enterprise computing system 108 may have trained the ML-AI models at block 502, or may obtain the trained ML-AI models from the sensing system that performed training at 502 for storing the ML-AI models in memory.

At block 506, the sensing system obtains one or more first vision ML-AI models associated with a product. For example, a sensing system may obtain the one or more vision ML-AI models trained in block 502 from the same memory the ML-AI models were stored in block 504. Additionally, and/or alternatively, the sensing system may obtain a different vision ML-AI model than the one or more ML-AI models trained at block 502, and from a different memory than the memory used for block 504. For example, the vision system 110 may obtain ML-AI models from a local memory of facility 102 which includes the one or more ML-AI models stored at block 504. The vision system 110 may obtain the same one or more ML-AI models stored at block 504, or may obtain a different ML-AI model. Vision system 110 may also obtain one or more ML-AI models from a memory of facility 104, user device 114, and/or enterprise computing system 108 via network 106. Similarly, when the sensing system is vision system 112 or enterprise computing system 108, the sensing system may obtain a different vision ML-AI model than the one or more ML-AI models trained at block 502, and from a different memory than the memory used for block 504.

At block 508, the sensing system obtains one or more images of a product label of the product. The product label may indicate a variable ink that changes colors based on environmental aspects. For example, when the sensing system is sensor system 300, vision capturing devices 302 may obtain images of a product label 606 and/or an individual 618 and processor 308 may provide these images or a representation of these images as an input to either the one or more pharmaceutical ML-AI models 312 or the one or more vision ML-AI models 314.

In some examples, the sensing system may be the first vision system 110 deployed in the supply chain facility 102, the second vision system 112 deployed in the storefront facility 104, or a cooperative combination of the first vision system 110 and the second vision system 112. In these examples, vision devices 602 of the first vision system 110 may obtain one or more images of a product label 606 in the supply chain facility, and/or vision devices 602 of the second vision system 112 may obtain one or more images of a product label 606 in the storefront facility 104.

In some instances, the enterprise computing system 108 obtains one or more images of a product label of the product, wherein the product label indicates a variable ink that changes colors based on environmental aspects. For example, the enterprise computing system 108 may obtain (e.g., retrieve, receive), from the sensing system, one or more images of a product label 606 associated with a product 608 and/or an individual 618, where the one or more images are captured by vision devices 302 of the sensing system.

At block 510, the sensing system determines condition information indicating a status of the product label based on executing the one or more first vision ML-AI models and the one or more images of the product label indicating the variable ink. For example, sensing system may be the vision system 110 and/or 112. The vision system 110 and/or 112 may input the images of the product label obtained in block 508 directly into the ML-AI models obtained at block 506, and the ML-AI models may determine the condition information that indicates a status of the product label (e.g., changed state, base state). Additionally, and/or alternatively, sensing system may obtain a representation of the images of the product label obtained in block 508 and input the representations to the one or more ML-AI models obtained at block 506 to determine the condition information that indicates a status of the product label (e.g., changed state, base state).

At block 512, the sensing system outputs an indicator indicating the status of the product label based on the condition information. For example, when the sensing system is vision system 112, the vision system 112 may output the indicator to the user device 114, vision system 110, and/or the computing devices of enterprise computing system 108, storefront facility 104, and/or supply chain facility 102 via the network 106. In some instances, when the sensing system includes the sensor system 300, the indicator may be output using the network interface 318 to provide the indicator to network 106. In some examples, the sensing system is the vision system 110, and the vision system 110 may output the indicator to the user device 114, vision system 112, and/or the computing devices of enterprise computing system 108, storefront facility 104, and/or supply chain facility 102 via the network 106. In some example, the sensing system is a cooperative combination of the vision system 110 and the vision system 112, and the combination may output the indicator to the user device 114 and/or the computing devices of enterprise computing system 108, storefront facility 104, and/or supply chain facility 102 via the network 106.

In some examples, at block 512, the enterprise computing system 108 may output the indicator indicating the status of the product label based on the condition information. For example, the enterprise computing system 108 may output the indicator to the user device 114, vision systems 110, 112, olfactory system 116, 118 (when present), and/or the computing devices of storefront facility 104 and/or supply chain facility 102 via the network 106.

Figure 8:
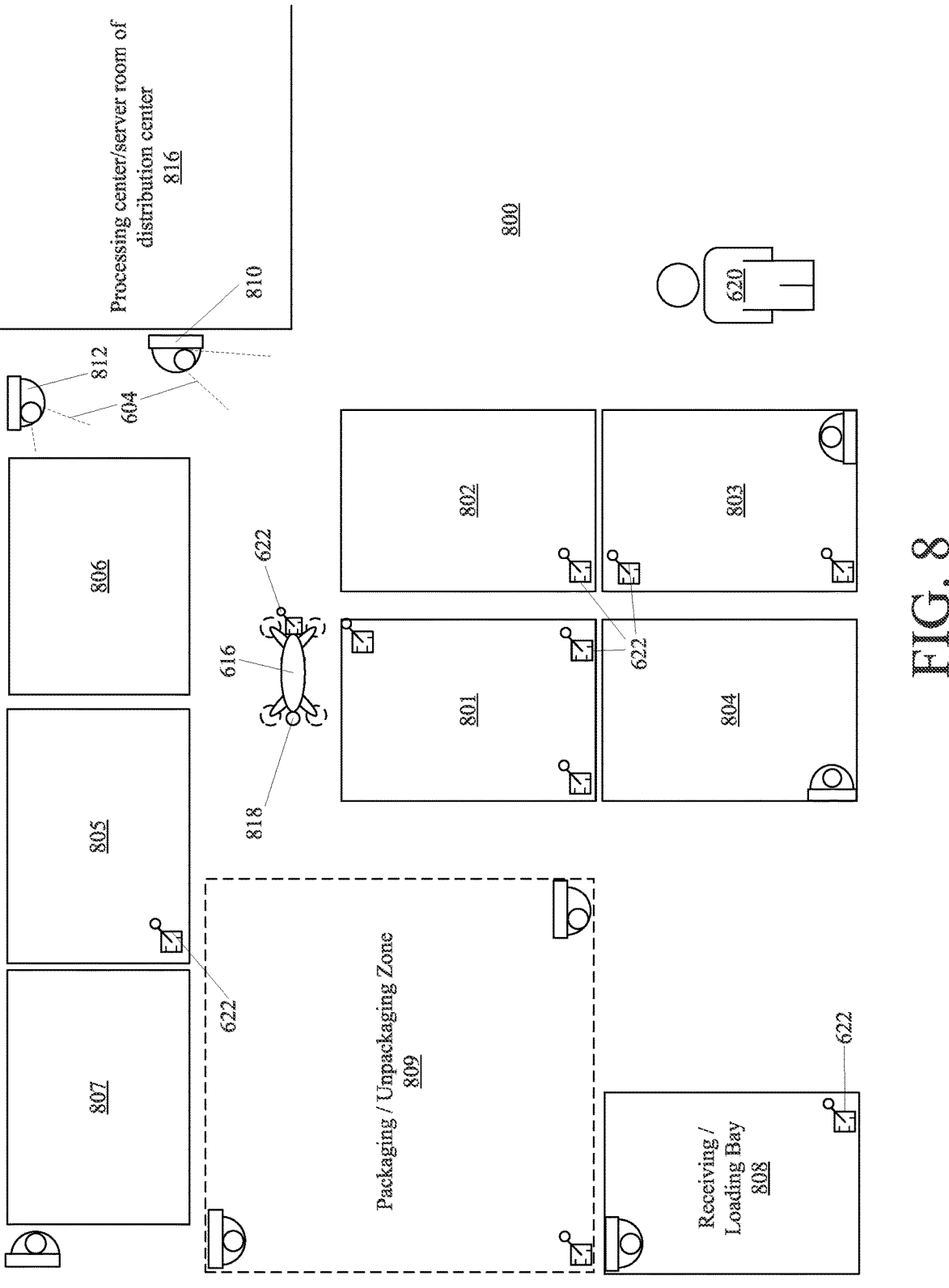
FIG. 8 depicts a schematic representation of a sensing system deployed in an exemplary environment in accordance with one or more examples of the present application.

As described above, in some examples, the vision devices 602 of the first and second vision systems 110, 112 may be ceiling mounted in an environment (e.g., environment 600, 800) strategically placed to see the tops and/or labels 606 of all the products 608. The shelves may be of a stair or pyramid shape so that all products 608 are seen by the vision devices 602. The cameras may be high definition (e.g., 8*k*, 6*k* cameras imaging/recording 33.2 million pixels and 8.3 million pixels, respectively) so that the vision devices 602 may zoom in and out on certain areas of the environment or product label 606 to make sure the vision devices 602 are getting a good indication of the Analog IoT color change of the variable ink sections (e.g., ink section 702*b*). In a distribution center (e.g., supply chain facility 102), a camera of vision devices 602 may be placed on opposite shelves and scan the front (e.g., visions devices 810*a* and 810*b* of FIG. 8), thereby obtaining one or more images of the product label 606 of the product 608 from a first viewpoint and one or more images of the product label 606 of the product 608 from a second viewpoint that is different from the first viewpoint. The products 608 may be placed single file on the shelves and wrapped in plastic packaging 610 with color changing and/or olfactory scent on a label in the front. The olfactory sensors (e.g., sensors 622) may be placed within 2 feet of the pallets and/or products 608 as shown in FIGS. 6 and 8. All totes may have these labels 606 as well. The labels 606 may be changed and in a protective coating so that no atmospheric conditions can touch them until they are ready to be used.

The vision systems 110, 112 may have edge models that are from enterprise computing system 108 that detect color changes due to temperature, humidity, and/or light changes that could affect the product 608 (e.g., a retail product and/or a pharmaceutical product). Different models (e.g., different models within the one or more vision models 314) may be used for ceilings and floors of an assigned range of values for atmospheric conditions. For example, a first model of the vision models 314 may use 70 degrees fahrenheit as a floor of a range and 95 degrees fahrenheit as a high of a range, and a second model of the vision models may use an indicator with a threshold humidity of 70% humidity. A third model of the vision models 314 may also determine that the product label 606 was in a high light environment and the color of a variable ink section 702*a* faded into variable ink section 702*b*.

In some examples, the labels 606, vision systems 110, 112, and/or olfactory systems 116, 118 have no batteries that need to be replaced, and labels 606 may have no electronics that need to be replaced, aiding protection of an enterprise organization's products and customers in an environmentally friendly way.

In some instances, the back-end server 108 includes olfactory models (e.g., olfactory models 316) for different changes in scent that may work together with the vision systems 110, 112 and vision models 314. These olfactory sensors (e.g., sensors 622) may be close to the products 608, placed on the bottom of the shelves every 2 feet. The olfactory models may include a model for determination of condition information based on a high scent, and when the scent fades or changes there could be an environmental condition or time that has changed. This determination may indicate that the product is approaching its end of life.

In some examples, the sensing system, based on the olfactory system 116, olfactory system 118, vision system 110, and/or vision system 112, may notify (e.g., via prompt) an employee (e.g., individual 120) of the determined indication of the status of product 608 so that the employee may put the product 608 in front of others for a quick sale, discard the product, or they may sell it with a discounted price depending on the product and/or pharmaceutical.

In some instances, once a product 608 has been flagged as improper because it is not within the ceiling or floor of a range for proper storage, a message may also be sent to the backend server 108 in addition to the notification of an employee (e.g., individual 120). The message may be used in decision analytics. When this product 608 was in another place (e.g., supply chain facility 102 or transit from facility 102 to facility 104), product 608 may have been next to other products that also had improper handling, and those other products may be flagged as well.

In some examples, the cameras of vision devices 602 and olfactory sensors 622 may work both independently and together, as they both have their own models determining condition information of product labels 606.

In some instances, pharmaceuticals (e.g., a subset of products 608) each have their own best environmental conditions baselines that may require their own models (e.g., pharmaceutical ML-AI models 312). All of the models 312 may be stored in a multi-modal AI. Models 312 may then be used to see the differences in the inks/scents and determine condition information of the labels 606.

In some examples, other enterprises may cooperate with the enterprise organization to use/apply labels 606 before shipping products 608 associated with label 606 to the enterprise organization, so that the other enterprises may be indirectly involved in the variable ink monitoring. These labels may be stored under perfect conditions before application, so that labels 606 are not tainted before being associated with (e.g., affixed to) the products 608. Once the seal of the packaging of label 606 is broken, a snapshot may be taken and put in an unsupervised ML-AI model to help train what the labels 606 look like in perfect conditions. The models may then have a baseline for future deviations.

For one example, some products may need to maintain a certain temperature or humidity range. Vision systems 110, 112 in respective facilities 102, 104 may look for characteristics of the variable ink that indicate the product was out of an environmental condition range (e.g., above a defined temperature threshold) for a period of time.

In some instances, the color of a variable ink section (e.g., ink section 702*b*) may change by geographic location. The models 312, 314 may be used aid in a determination of a path product 608 took based on the colors represented in different chromatics. For example, if a product 608 started in Europe and shipped to the United States, there might be environmental conditions that exist that could change the color of a small label (e.g., changes only an IR camera can see).

In some examples, the label (e.g., label 700) may be placed on a human or user such as a patient, person, customer, and/or employee. For example, referring to FIG. 6, a label 620 (e.g., a variable ink label, marker, or patch) may be placed onto an individual 618 such as an employee. The variable ink on the label 620 may change based on a temperature of the individual 618. For instance, a baseline condition of the variable ink may be associated with the individual 618 at a normal body temperature (e.g., 98.6 degrees fahrenheit). If the individual 618 has a fever (e.g., above 100 degrees fahrenheit), the variable ink may change colors (e.g., from a baseline color to a new color). A sensing system (e.g., the vision device 602) may obtain an image of the product label and perform process 400 to output an indicator indicating the status of the individual 618. For instance, at block 406, the sensing system may determine condition information indicating a status of the product label (e.g., the label 620) based on inputting the image of the label into the vision ML-AI models. At block 408, the sensing system may output an indicator such as display, on the user device 114, that an employee is sick. The sensing system may therefore improve and/or assist the sustainability of processes for monitoring human health (e.g., by providing an analog option alternatively and/or in addition to the use of electronic batteries and wiring), which may in turn further the enterprise organization's environmental goals, such as their ESG criteria.

Additionally, and/or alternatively, the sensing system may use one or more additional sensors such as humidity sensors, audio sensors, and/or other sensors that are described above to determine the condition information. For instance, similar to using the olfactory sensor, the sensing system may determine a humidity (e.g., perspiration/cold sweats) associated with the individual 618 and/or audio information of the individual 618 (e.g., audio of the individual 618 coughing). Based on the sensor information and/or the image of the product label, the sensing system may determine condition information indicating a condition of the individual 618 (e.g., whether the individual is sick). For instance, the sensing system may use one or more ML-AI models (e.g., health condition machine learning models/datasets) to determine the condition of the individual 618. Examples of using ML-AI models with the humidity information from the humidity sensors, audio information from the audio sensors, image representations from the image capturing devices, and/or other sensors to determine the condition of the individual 618 is described in further detail in U.S. patent application Ser. No. 16/886,464 (Titled: SYSTEMS AND METHODS FOR DETERMINING AND USING HEALTH CONDITIONS BASED ON MACHINE LEARNING ALGORITHMS AND A SMART VITAL DEVICE), filed on May 28, 2020, which is incorporated by reference herein in its entirety.

A number of implementations have been described. Nevertheless, it will be understood that additional modifications may be made without departing from the scope of the inventive concepts described herein, and, accordingly, other examples are within the scope of the following claims. For example, it will be appreciated that the examples of the application described herein are merely exemplary. Variations of these examples may become apparent to those of ordinary skill in the art upon reading the foregoing description. The inventor expects skilled artisans to employ such variations as appropriate, and the inventor intends for the application to be practiced otherwise than as specifically described herein. Accordingly, this application includes all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

It will further be appreciated by those of skill in the art that the execution of the various machine-implemented processes and steps described herein may occur via the computerized execution of processor-executable instructions stored on a non-transitory computer-readable medium, e.g., random access memory (RAM), read-only memory (ROM), programmable read-only memory (PROM), volatile, nonvolatile, or other electronic memory mechanism. Thus, for example, the operations described herein as being performed by computing devices and/or components thereof may be carried out by according to processor-executable instructions and/or installed applications corresponding to software, firmware, and/or computer hardware.

The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the application and does not pose a limitation on the scope of the application unless otherwise claimed. No language in the specification should be construed as indicating any non-claimed element as essential to the practice of the application.

The invention claimed is:

1. A system, comprising:

one or more vision capturing devices configured to obtain one or more images of a product label of a product, wherein the product label indicates a variable ink that changes colors based on environmental aspects;

one or more sensor system computing devices configured to:

access, via an enterprise computing system, one or more first machine learning-artificial intelligence (ML-AI) models associated with the product;

determine condition information indicating a status of the product label based on the one or more first ML-AI models, a determination of at least one environmental condition the product label was exposed to from a plurality of potential environmental conditions, and the one or more images of the product label indicating the variable ink; and provide, to a user device, an indicator indicating the status of the product label based on the condition information; and the user device, wherein the user device is configured to:

receive the indicator indicating the status of the product label; and cause display of a prompt indicating a condition of the product.

2. The system of claim 1, wherein the prompt indicates to sell the product at a discounted price or discard the product.

3. The system of claim 1, wherein the system further comprises one or more olfactory sensors configured to obtain olfactory information indicating a scent of the product, and the one or more sensor system computing devices are further configured to:

access, via the enterprise computing system, one or more second ML-AI models associated with the product; and determine the condition information indicating the status of the product label further based on the one or more second ML-AI models and the olfactory information.

4. The system of claim 1, wherein the variable ink is a thermochromatic ink that changes color based on a temperature range, and wherein product label training information for the one or more first ML-AI models comprises one or more images of thermochromatic ink product labels.

5. A method, comprising:

obtaining one or more vision machine learning-artificial intelligence (ML-AI) models associated with a product;

obtaining one or more images of a product label of the product, wherein the product label indicates a variable ink that changes colors based on environmental aspects;

determining condition information indicating a status of the product label based on the one or more vision ML-AI models, a determination of at least one environmental condition the product label was exposed to from a plurality of potential environmental conditions, and the one or more images of the product label indicating the variable ink; and outputting an indicator indicating the status of the product label based on the condition information.

6. The method according to claim 5, wherein outputting the indicator indicating the status of the product label further comprises:

providing, to a user device, the indicator indicating the status of the product label, wherein the user device causes display of a prompt indicating the status of the product label, wherein the prompt indicates to sell the product at a discounted price or discard the product.

7. The method according to claim 5, further comprising:

obtaining one or more olfactory ML-AI models associated with the product; and obtaining, using one or more olfactory sensors, olfactory information indicating a scent of the product, and wherein determining the condition information indicating the status of the product label is further based on the one or more olfactory ML-AI models and the olfactory information.

8. The method according to claim 7, wherein determining the condition information indicating the status of the product label comprises:

inputting one or more representations associated with the one or more images into the one or more vision ML-AI models to determine vision ML-AI information;

inputting the olfactory information into the one or more olfactory ML-AI models to determine olfactory ML-AI information; and determining the condition information indicating the status of the product label based on the vision ML-AI information and the olfactory ML-AI information.

9. The method according to claim 8, wherein the vision ML-AI information is a first condition confidence value that is output from the one or more vision ML-AI models, wherein the olfactory ML-AI information is a second condition confidence value that is output from the one or more olfactory ML-AI models, and wherein determining the condition information comprises determining the condition information as a weighted average of the first condition confidence value and the second condition confidence value.

10. The method according to claim 5, further comprising:

training the one or more vision ML-AI models based on product label training information indicating statuses of a plurality of product labels; and storing the trained one or more vision ML-AI models in memory, and wherein obtaining the one or more vision ML-AI models comprises retrieving the trained one or more vision ML-AI models from memory.

11. The method according to claim 10, wherein the product label training information comprises a plurality of images of the plurality of product labels, wherein at least one of the plurality of images indicates a baseline condition of a first product label prior to being applied to any products, and wherein the one or more vision ML-AI models comprises an unsupervised ML-AI model.

12. The method according to claim 10, wherein the variable ink is a photochromic ink that changes colors based on temperature or exposure to sunlight, and wherein the product label training information comprises one or more images of photochromic ink product labels.

13. The method according to claim 10, wherein the variable ink is a glow-in-the-dark ink that changes colors based on absorbing light and glowing in darkness, and wherein the product label training information comprises one or more images of glow-in-the-dark ink product labels.

14. The method according to claim 10, wherein the variable ink is a fluorescing ink that absorbs ultraviolet (UV) light and re-emits the UV light within a visible spectrum, and wherein the product label training information comprises one or more images of fluorescing ink product labels.

15. The method according to claim 5, wherein the one or more vision ML-AI models comprise a pharmaceutical vision ML-AI model associated with a pharmaceutical medication and a retail vision ML-AI model associated with one or more retail items, and wherein the method further comprises:

determining, based on the one or more images, whether the product is the one or more retail items or the pharmaceutical medication, and wherein determining the condition information is further based on whether the product is the one or more retail items or the pharmaceutical medication.

16. The method according to claim 5, wherein the one or more vision ML-AI models comprise a first pharmaceutical vision ML-AI model associated with a first type of pharmaceutical medication and a second pharmaceutical vision ML-AI model associated with a second type of pharmaceutical medication, and wherein the method further comprises:

training the first pharmaceutical vision ML-AI model based on a plurality of first images of one or more first product labels at a first baseline condition; and training the second pharmaceutical vision ML-AI model based on a plurality of second images of one or more second product labels at a second baseline condition that is different from the first baseline condition.

17. The method according to claim 5, wherein obtaining the one or more vision ML-AI models further comprises receiving, from an enterprise computing system, the one or more vision ML-AI models that are trained by the enterprise computing system, and wherein obtaining the one or more images of the product label comprises capturing the one or more images of the product label.

18. The method according to claim 17, wherein outputting the indicator indicating the status of the product label comprises providing the indicator to the enterprise computing system, and wherein the method further comprises:

receiving, from the enterprise computing system, identification information indicating one or more additional products that have the same status as the product.

19. The method according to claim 5, wherein the one or more images comprise a first image of the product label of the product from a first viewpoint and a second image of the product label of the product from a second viewpoint that is different from the first viewpoint.

20. A non-transitory computer-readable medium having processor-executable instructions stored thereon, wherein the processor-executable instructions, when executed by one or more controllers, facilitate:

obtaining one or more vision machine learning-artificial intelligence (ML-AI) models associated with a product;

obtaining one or more images of a product label of the product, wherein the product label indicates a variable ink that changes colors based on environmental aspects;

determining condition information indicating a status of the product label based on the one or more vision ML-AI models, a determination of at least one environmental condition the product label was exposed to from a plurality of potential environmental conditions, and the one or more images of the product label indicating the variable ink; and outputting an indicator indicating the status of the product label based on the condition information.

* * * * *